US005194595A

United States Patent [19]

Wathen

[11] Patent Number: 5,194,595

[45] Date of Patent: Mar. 16, 1993

[54] CHIMERIC GLYCOPROTEINS CONTAINING IMMUNOGENIC SEGMENTS OF THE GLYCOPROTEINS OF HUMAN RESPIRATORY SYNCYTIAL VIRUS

[75] Inventor: Michael W. Wathen, Portage, Mich.

[73] Assignee: The Upjohn Company, Kalamazoo, Mich.

[21] Appl. No.: 543,780

[22] PCT Filed: Oct. 31, 1988

[86] PCT No.: PCT/US89/03784

§ 371 Date: Jun. 20, 1990

§ 102(e) Date: Jun. 20, 1990

[87] PCT Pub. No.: WO87/04185

PCT Pub. Date: Jul. 16, 1987

Related U.S. Application Data

[63] Continuation-in-part of Ser. No. 137,387, Dec. 23, 1987, abandoned.

[51] Int. Cl.$^5$ ...................... C07K 13/00; C12N 15/45; C12P 21/02; A61K 37/02

[52] U.S. Cl. ................................ 530/395; 435/172.3; 435/69.7; 424/89

[58] Field of Search .................... 435/69.1, 236, 320.1, 435/172.3; 536/27; 530/395

[56] References Cited

U.S. PATENT DOCUMENTS 4,855,224 8/1989 Berman et al. ........................ 435/5

FOREIGN PATENT DOCUMENTS

WO87/04185 7/1987 World Int. Prop. O. .

OTHER PUBLICATIONS

Brideau et al., *J. Gen. Virol.*, vol. 70, 1989, pp. 2637-2644.

Sullender et al., *Virology*, vol. 178, 1990, pp. 195-203.

Johnson et al., *J. Virol.*, vol. 61, 1987, pp. 3163-3166.

Prince et al., *Am. J. Pathol.*, vol. 93, 1978, pp. 771-791.

Walsh et al., *Infect. Immun.*, vol. 43, 1984, pp. 756-758.

Prince et al., *Infect. Immun.*, vol. 42, 1983, pp. 81-87.

Walsh et al., *J. Infect. Diseases*, vol. 155, 1987, pp. 1198-1204.

Ball, L. A., et al., "Expression of the Major Glycoprotein G of Human Respiratory Syncytial Virus from Recombinant Vaccinia Virus Vectors", Jan. 1986, Proc. Natl. Acad. Sci. U.S.A., 83:246-250.

Olmstead, R. A., et al., "Expression of the F Glycoprotein of Respiratory Syncytial Virus by a Recombinant Vaccinia Virus: Comparison of the Individual Contributions of the F and G Glycoproteins to Host Immunity", Oct. 1986, Proc. Natl. Acad. Sci. U.S.A., 83:7462-7466.

Stott, E. J., et al., "Human Respiratory Syncytial Virus Glycoprotein G Expressed from a Recombinant Vaccinia Virus Vector Protects Mice Against Live-Virus Challenge", Nov. 1986, J. Virol. 60(2):607-613.

Walsh, E. E., et al., "Immunization with Glycoprotein Subunits of Respiratory Syncytial Virus to Protect Cotton Rats Against Viral Infection", Jun. 1987, J. Infect. Dis. 155(6):1198-1204.

Wertz, G. W., et al., "Expression of the Fusion Protein of Human Respiratory Syncytial Virus from Recombinant Vaccinia Virus Vectors and Protection of Vaccinated Mice", Feb. 1987, J. Virol. 61(2):293-301.

Elango, N., et al., "Resistance to Human Respiratory Syncytial Virus (RSV) Infection Induced by Immunization of Cotton Rats with a Recombinant Vaccinia Virus Expressing the RSV G Glycoprotein", Mar. 1986, Proc. Natl. Acad. Sci. U.S.A., 83:1906-1910.

Wertz, G. W., et al., "Nucleotide Sequence of the G Protein Gene of Human Respiratory Syncytial Virus Reveals an Unusual Type of Viral Membrane Protein", Jun. 1985, Proc. Natl. Acad. Sci. U.S.A. 82:4075-4079.

Johnson, Jr., R. J., et al., "Antigenic Relatedness Between Glycoproteins of Human Respiratory Syncytial Virus Subgroups A and B: Evaluation of the Contributions of F and G Glycoproteins to Immunity", Oct. 1987, J. Virol. 61(10):3163-3166.

Moss, B., "Vaccine Against Respiratory Syncytial Virus is Recombinant Vaccinia Virus Esp. Vaccinia-RSV G and F Glycoprotein Viruses", 26 Aug. 1986, Dialog Information Services, File 351, World Patent Index 81-89, Dialog Accession No. 4,315,328, U.S. 6,849,299, A.

Collins et al., *PNAS* vol. 81, 1984, pp. 7683-7687.

*Primary Examiner*—Richard A. Schwartz
*Assistant Examiner*—James Ketter
*Attorney, Agent, or Firm*—Mark Deluca; Donald Corneglio

[57] ABSTRACT

This invention encompasses DNA compositions encoding novel chimeric glycoproteins which are useful for preparing virus specific immune responses against human respiratory syncytial virus. The DNA compositions include structural genes coding for the glycoproteins and expression and replication plasmids containing the structural genes. Host cells transformed with the above DNA compositions, vaccines made from the glycoproteins and methods for protecting humans by inoculation with said vaccines are also part of this invention.

4 Claims, No Drawings

CHIMERIC GLYCOPROTEINS CONTAINING IMMUNOGENIC SEGMENTS OF THE GLYCOPROTEINS OF HUMAN RESPIRATORY SYNCYTIAL VIRUS

This is a continuation-in-part of application Ser. No. 07/137,387, filed Dec. 23, 1987, now abandoned.

FIELD OF THE INVENTION

This invention encompasses DNA compositions encoding novel chimeric glycoproteins which are useful for preparing virus specific immune responses against human respiratory syncytial virus, HRSV. The DNA compositions include structural genes coding for the glycoproteins and expression and replication plasmids containing the structural genes. Host cells transformed with the above DNA compositions, vaccines made from the glycoproteins and methods for protecting humans by inoculation with said vaccines are also part of this invention.

BACKGROUND

HRSV was discovered in 1956 and is found worldwide. It causes upper and lower respiratory tract disease particularly in infants and young children. About 30 percent of hospitalized young children with acute respiratory disease have respiratory syncytial virus infection. In older children and adults the disease is milder. In infants this severe illness often requires hospitalization.

Infections with respiratory syncytial virus are referable to all segments of the respiratory tract, are usually associated with fever, cough, runny nose, and fatigue, and are diagnosed clinically as bronchitis, bronchiolitis, pneumonia, croup, or viral infection. In older children and adults the virus is generally limited to replication in the upper respiratory tract. Infants may be more severely involved when the virus extends into the lungs. Lung damage can be permanent.

Primary infection with respiratory syncytial virus occurs early in life, usually before 4 years of age. Among children, illness caused by this virus tends to occur at least once each year in rather sharply defined outbreaks of several months duration. Epidemics are sharply circumscribed, generally for 3 to 5 months. In family studies, children in early school years frequently introduce the virus into the home, infecting younger members of the family more severely than other family members. The clinical consequence of infection is most severe on first experience and becomes milder in older individuals who are immunologically experienced.

Secondary effects of respiratory syncytial virus can range from inapparent infection to severe pneumonia and death. Inflammation of the respiratory tract is responsible for most symptoms. Complete recovery in most cases occurs in one to three weeks with the production of antibody which appears to persist throughout life. In the United States about 30 percent of 1-year-old infants and 95 percent of 5-year-old children have circulating respiratory syncytial virus antibody. Reinfections in older infants, children, and adults with antibody are mostly mild upper respiratory illnesses in the form of colds.

Although low yields of virus in cell culture have hindered HRSV research, the virus has been well studied. HRSV is a paramyxovirus containing a single negative strand of RNA which is transcribed into 10 predominantly monocistronic messengers. The messengers have been isolated and translated in vitro. The products have been characterized by gel electrophoresis, peptide mapping and immuno-precipitation as being similar to structural proteins isolated from virions. The structural proteins include a major nucleocapsid protein (N; MW ca. 42,000), a nucleocapsid phosphoprotein (P; MW ca. 34,000), a large nucleocapsid protein (L; MW ca. 200,000), an envelope matrix protein (M; MW ca. 26,000), a matrix glycoprotein (ca. 22,000) and two envelope glycoproteins, the fusion glycoprotein (F; MW ca. 68,000 to 70,000) and a second, methionine poor glycoprotein (G; MW ca. 84,000 to 90,000). In addition, a virally encoded protein of about 9,500 daltons and other small proteins are known to be present in infected cells, Collins, et al., Identification of a tenth mRNA of HRSV and assignment of polypeptides to the 10 viral genes, J. of Virol. 49:572-578 (1984) and references cited therein. Additional work describing the molecular biology of HSRV includes: (1) Collins, et al., Nucleotide Sequence of the gene encoding the fusion (F) glycoprotein of human respiratory syncytial virus, Proc. Natl. Acad. Sci., USA, 81:7683-7687 (December 1984) disclosing the gene sequence for the F glycoprotein; (2) Collins, et al., The 1A Protein Gene of Human Respiratory Syncytial Virus: Necleotide Sequence of the mRNA and a Related Polycistronic Transcript, Virology, 141:283-291 (1985) disclosing the gene sequence for the 1A protein; (3) Collins, et al., The Envelope-Associated 22K Protein of Human Respiratory Syncytial Virus: Nucleotide Sequence of the mRNA and a Related Polytranscript, J. of Virol., 54(No. 1):65-71 (April 1985) disclosing the gene sequence for the 22K protein; (4) Wertz, et al., Nucleotide sequence of the G protein gene of human respiratory syncytial virus reveals an unusual type of viral membrane protein, Proc. Natl. Acad. Sci., USA, 82:4075-4079 (June 1985) disclosing the gene sequence for the G glycoprotein; and (5) Collins, et al., Correct Sequence for the Major Nucleocapsid Protein mRNA of Respiratory Syncytial Virus, Virology, 146:69-77 (1985) disclosing the gene sequence for the ∞ protein.

The F and G glycoproteins of HRSV have similar counterparts in the other paramyxoviruses. Like HRSV, other paramyxoviruses have an F glycoprotein which is associated with fusion of cell membranes, P. W. Choppin and A. Scheid, Rev. Infect. Dis. 2:40-61, (1980); Merz, et al., J. Exp. Med. 151:275-288, (1980). The active paramyxovirus F protein consists of two disulfide-linked subunits, $F_1$ and $F_2$, which are generated from an inactive precursor ($F_0$) by a specific internal cleavage by cellular proteases, Scheid and Choppin, Virol. 80:54-66 (1977). The second major glycoprotein for most paramyxoviruses is termed the HN protein, and is associated with the hemagglutinin and neuraminidase activities of these viruses. Although the HRSV G protein does not have the above enzymatic activities, both the G and HN glycoproteins are associated with attachment of virus. Also, these glycoproteins are structurally similar in that they have an unusual hydrophobic signal/anchor region at their amino-terminus, Wertz, et al., PNAS 82:4075-4079 (1985); Elango, et al., J. Virol. 57:481-489 (1986).

There are no available effective vaccines to combat HRSV. Multiple attempts have been made to obtain an effective vaccine against HRSV. Friedewald, et al., Journal of the American Medical Association, 204:690-694 (May 20, 1968), describe the propagation of respiratory syncytial virus in bovine embryonic kidney tissue culture. Virus grown at 34° C. or 28° C. did not decrease in infectivity or virulence. HRSV grown at 26° C., while associated with a decrease in infectivity for adults, could not be considered for use in prevention of infection in adults since the virus had limited infectivity and was poorly immunogenic.

Kim, et al., Pediatrics, 48:745-755 (November 1971) disclose that inactivated respiratory syncytial virus vaccine prepared from virus grown at 26° C. stimulated the development of high levels of serum antibody in infants and children from 6 months to 13 years in age but did not prevent infection.

McIntosh, et al., Pediatric Research, 8:689-696 (1974) discuss two experimental live respiratory syncytial virus vaccines, one prepared from virus grown at 26° C. and the other, prepared from a temperature sensitive mutant which grew well at 32° C. and not at all at 37° C. or higher. The first vaccine was unsatisfactory as it did not protect against infection when the interval between vaccination and challenge was greater than 4 months. The second vaccine was also unsatisfactory in that it apparently lost its temperature sensitivity in some vaccinees.

Craighead, Journal of Infectious Diseases, 131:749-753 (June 1975) discusses tests conducted in 1966 wherein several groups of investigators tested in infants and young children a formaldehyde-treated, alum-precipitated virus grown in tissue culture. Upon subsequent exposure to wild virus the vaccine recipients exhibited an accentuated pattern of respiratory tract disease. Craighead concludes that immunization with formaldehyde treated virus enhanced the severity of the disease.

Wright, et al., Journal of Pediatrics, 88:931-936 (June 1976) describe the evaluation in infants of a temperature sensitive live attenuated respiratory syncytial vaccine. While this vaccine when administered at a dosage level sufficiently high to infect all seronegative infants caused mild upper respiratory illness, lowering the dose did not achieve an acceptable level of infectivity. The virus was also genetically unstable as there was evidence of loss of temperature sensitivity in one vaccinee. There was no evidence for potentiation of natural illness with this vaccine and reinfection occurred among vaccinees.

U.S. Pat. Nos. 4,122,167 and 4,145,252 describe a method for attenuating virions by serial passage through human diploid lung fibroblasts and U.S. Pat. No. 4,517,304 discloses a method for producing immunogenically active HRSV proteins upon the cell membranes of susceptible cells grown in culture. These cells are then injected into a host to elicit an immune response.

INFORMATION DISCLOSURE STATEMENT

The recombinant vaccinia virus expression system is known to separately express the G and F glycoproteins of HRSV, Ball, et al., Expression of the Major Glycoprotein G of Human Respiratory Syncytial Virus from Recombinant Vaccinia Virus Vectors, P.N.A.S., USA, 83:246-250 (1986) and Olmsted, et al., Expression of the F Glycoprotein of Respiratory Syncytial Virus by a Recombinant Vaccinia Virus: Comparison of the Individual Contributions of the F and G Glycoproteins to Host Immunity, P.N.A.S., USA, 83:7462-7466 (1986). These two glycoproteins were also demonstrated to induce immunoprotection in mammals against a live HRSV virus challenge, Stott, et al., Human Respiratory Syncytial Virus Glycoprotein G Expressed from Recombinant Vaccinia Virus Vector Protects Mice Against Live-virus Challenge, Journal of Virology 67:607-613 (1986); Walsh, et al., Immunization with Glycoprotein Subunits of Respiratory Syncytial Virus to Protect Cotton Rats Against Viral Infection, Journal of Infectious Diseases, 1198-1204 (1987); Wertz, et al., Expression of the Fusion Protein of Human Respiratory Syncytial Virus from Recombinant Vaccinia Virus Vectors and Protection of Vaccinated Mice, Journal of Virology, 293-301 (1987); Elango, et al., Resistance to Human Respiratory Syncytial Virus (RSV) Infection Induced by Immunization of Cotton Rats with a Recombinant Vaccinia Virus Expressing the RSV G Glycoprotein, Proc. Natl. Acad. Sci. USA, 1906-1910 (1986).

SUMMARY OF THE INVENTION

This invention encompasses a polypeptide comprising a signal sequence and at least one immunogenic fragment from both human respiratory syncytial virus glycoproteins F and G. The use of this protein as a vaccine, methods to prevent HRSV-related disease and preparation of this protein using recombinant techniques are also part of this invention.

DETAILED DESCRIPTION

The following defined terms are used in this specification. The phrase "cell culture" refers to the containment of growing cells derived from either a multicellular plant or animal which allows for the cells to remain viable outside the original plant or animal. The term "downstream" identifies sequences proceeding farther in the direction of expression; for example, the coding region is downstream from the initiation codon. The term "microorganis.n" includes both single cellular prokaryote and eukaryote organisms such as bacteria, actinomycetes and yeast. The term "operon" is a complete unit of gene expression and regulation, including structural genes, regulator genes and control elements in DNA recognized by regulator gene product. The term "plasmid" refers to an autonomous self-replicating extrachromosomal circular DNA and includes both the expression and nonexpression types. Where a recombinant microorganism or cell culture is described as hosting an expression plasmid the phrase "expression plasmid" includes both extrachromosomal circular DNA and DNA that has been incorporated into the host chromosome(s). Where a plasmid is being maintained by a host cell, the plasmid is either being stably replicated by the cells during mitosis as an autonomous structure or as an incorporated portion of the host's genome. The term "promoter" is a region of DNA involved in binding the RNA polymerase to initiate transcription. The phrase "DNA sequence" refers to a single or double stranded DNA molecule comprised of nucleotide bases, adenosine, thymidine, cytosine and guanosine. The phrase "essentially pure" refers to a composition of protein that contains no paramyxovirus protein other than the desired recombinant chimeric glycoprotein. Although the essentially pure proteins may be contaminated with low levels of host cell constituents, the protein is devoid of contaminating structural and non-structural viral protein produced by replicating paramyxoviruses. The phrase "suitable host" refers to a cell culture or microorganism that is compatible with a recombinant plasmid and will permit the plasmid to replicate, to be incorporated into its genome or to be expressed. The term "upstream" identifies sequences proceeding in the opposite direction from expression; for example, the bacterial promoter is upstream from the transcription unit, the initiation codon is upstream from the coding region.

This invention involves a series of molecular genetic manipulations that can be achieved in a variety of known ways. The manipulations can be summarized as obtaining a cDNA of the protein, the cloning and replication of the cDNA in E. coli and the expression of the desired cDNA in a suitable host. The following descriptions will detail the various methods available to express the protein and are followed by specific examples of preferred methods. The specific sequence and base numbering positions for a particular polypeptide, glycoprotein FG, is given in Chart 9.

Generally, the nomenclature and general laboratory procedures required in this invention can be found in Maniatis, et al., Molecular Cloning A Laboratory Manual, Cold Spring Harbor Laboratory, Cold Spring Harbor, N.Y. 1982 (Maniatis).

All *E. coli* strains are grown on Luria broth (LB) with glucose, Difco's Antibiotic Medium #2 and M9 medium supplemented with glucose and acid-hydrolyzed casein amino acids. Strains with resistance to antibiotics were maintained at the drug concentrations described in Maniatis. Transformations were performed according to the method described by Rowekamp and Firtel, Dev. Biol., 79:409–418 (1980).

All enzymes were used according to the manufacturer's instructions. Transformants were analyzed by colony hybridization as described in Grunstein and Wallis, Methods in Enzymology, 68:379–388.

After hybridization, the probes are removed and saved, and the filters are washed in 0.1% SDS, 0.2×SSC for a total of 3 hours with 5 changes of 400 ml each. Filters are thoroughly air dried, mounted, and autoradiographed using Kodak X-OMAT AR film and Dupont Cronex Lightnening Plus intensifying screens for 16 hours at −70° C.

For sequencing of plasmids, purified plasmid DNA is prepared according to the methods described in Maniatis. End-labeled DNA fragments are prepared and analyzed by the chemical sequencing methods of Maxam and Gilbert with modifications described by Collins and Wertz, J. Virol. 54:65–71 (1985).

Nucleotide sizes are given in either kilobases (kb) or basepairs (bp). These are estimates derived from agarose gel electrophoresis.

The first step in obtaining expression of protein is to obtain the DNA sequence coding for the protein from cDNA clones. This sequence is then cloned into an expression plasmid which is capable of directing transcription of the gene and allowing efficient translation of the transcript. The library method for obtaining cDNA encoding protein has been described generally in Maniatis, and specifically in Collins and Wertz, cDNA Cloning and Transcriptional Mapping of Nine Polyadenylated RNAs Encoded by the Genome of HRSV, Proc. Natl. Acad. USA 80: 3208–3212 (1983) and the related documents Elango, N., et al., Resistance to Human Respiratory Syncytial Virus (RSV) Infection Induced by Immunization of Cotton Rats with a Recombinant Vaccinia Virus Expressing the RSV G Glycoprotein, Proc. Natl. Acad. Sci. USA, 1906–1910 (1986) and Olmstead R. A. et al., Expression of the F Glycoprotein of Respiratory Syncytial Virus by a Recombinant Vaccinia Virus: Comparison of the Individual Contributions of the F and G glycoproteins to Host Immunity, Proc. Natl. Acad. Sci. USA, 7462–7466 (1986).

Clones are prepared by inserting the cDNA into PstI cleaved pBR322 to which homopolymer tracts of dGTP have been enzymatically added to the 3′ ends at the cleavage site. Homopolymer tracts of dCTP are enzymatically added to the 3′ termini of the cDNA molecules according to the methods described by Maniatis. Ideally, 10–30 residues of dCTP or dGTP should be added to maximize cloning efficiency. The cDNA and plasmid are annealed together and transformed into E. coli. The clones containing full length cDNA are detected by probes of labeled viral cDNA or oligonucleotides complementary to portions of the gene sequences, followed by restriction enzyme analysis and DNA sequencing.

Oligonucleotides are chemically synthesized according to the solid phase phosphoramidite triester method first described by Beaucage and Caruthers, Tetrahedron Letters, 22(20): 1859–1862 (1981) using an automated synthesizer, as described in Needham-VanDevanter, et al., Nucleic Acids Res., 12:6159–6168 (1984). Purification of oligonucleotides is by either native acrylamide gel electrophoresis or by anion-exchange HPLC as described in Pearson and Regnier, J. Chrom., 255:137–149 (1983).

The sequence of the synthetic oligonucleotides can be verified using the chemical degradation method of Maxam and Gilbert, Grossman and Moldave, eds., Academic Press, New York, Methods in Enzymology, 65:499–560 (1980).

To obtain high level expression of a cloned gene in a prokaryotic system, it is essential to construct expression vectors which contain, at the minimum, a strong promoter to direct mRNA transcription, a ribosome binding site for translational initiation, and a transcription terminator. Examples of regulatory regions suitable for this purpose are the promoter and operator region of the *E. coli* tryptophan biosynthetic pathway as described by Yanofsky, Kelley, and Horn, J. Bacteriol., 158:1018–1024 (1984) and the leftward promoter of phage lambda ($P_L$) as described by Herskowitz and Hagen, Ann. Rev. Genet., 14:399–445 (1980).

The proteins produced in E. coli will not fold properly due to the presence of cysteine residues and to the lack of suitable post-translational modifications. During purification from *E. coli*, the expressed proteins must first be denatured and then renatured. This can be accomplished by solubilizing the *E. coli* produced proteins in guanidine HCl and reducing all the cysteine residues with β-mercaptoethanol. The protein is then renatured either by slow dialysis or by gel filtration, U.S. Pat. No. 4,511,503.

Detection of proteins is achieved by methods known in the art such as radioimmunoassays, or Western blotting techniques or immunoprecipitation. Purification from *E. coli* can be achieved following procedures described in U.S. Pat. No. 4,511,503.

Expression of heterologous proteins in yeast is well known and described. Methods in Yeast Genetics, Sherman, et al., Cold Spring Harbor Laboratory, (1982) is a well recognized work describing the various methods used to produce proteins in yeast.

For high level expression of a gene in yeast, it is essential to connect the gene to a strong promoter system as in the prokaryote and to also provide efficient transcription termination/polyadenylation sequences from a yeast gene. Examples of useful promoters include GAL1,10, Johnston and Davis, Mol. and Cell. Biol., 4:1440-1448, 1984), ADH2, Russell, et al., J. Biol. Chem. 258:2674-2682, 1983), PHO5, EMBOJ. 6:675-680, (1982), and MFα1. A multicopy plasmid with a selective marker such as Lue-2, URA-3, Trp-1, or His-3 is also desirable. The MFα1 promoter is preferred. The MFα1 promoter, in a host of the α mating-type is constitutive, but is off in diploids or cells with the a mating-type. It can, however, be regulated by raising or lowering temperature in hosts which have a ts mutation at one of the SIR loci. The effect of such a mutation at 35° C. on an α type cell is to turn on the normally silent gene coding for the a mating-type. The expression of the silent a mating-type gene, in turn, turns off the MFα1 promoter. Lowering the temperature of growth to 27° C. reverses the whole process, i.e., turns the a mating-type off and turns the MFα1 on, Herskowitz and Oshima, The Molecular Biology of the Yeast Saccharomyces, Strathern, Jones, and Broach, eds., Cold Spring Harbor Lab., Cold Spring Harbor, N.Y. 181-209, (1982).

The polyadenylation sequences are provided by the 3'-end sequences of any of the highly expressed genes, like ADH1, MFα1, or TPI, Alber and Kawasaki, J. of Mol. and Appl. Genet. 1:419-434, (1982).

A number of yeast expression plasmids like YEp6, YEp13, YEp24 can be used as vectors. A gene of interest can be fused to any of the promoters mentioned above, and then ligated to the plasmids for expression in various yeast hosts. These plasmids have been fully described in the literature, Botstein, et al., Gene, 8:17-24, (1979); Broach, et al., Gene, 8:121-133, (1979).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by Beggs, Nature (London), 275:104-109 (1978); and Hinnen, et al., Proc. Natl. Acad. Sci. USA, 75:1929-1933 (1978). The second procedure does not involve removal of the cell wall. Instead the cells are treated with lithium-chloride or acetate and PEG and put on selective plates, Ito, et al., J. Bact., 153:163-168, (1983).

The cDNA can be ligated to various expression vectors for use in transforming host cell cultures. The vectors all contain gene sequences to initiate transcription and translation of the proteins that are compatible with the host cell to be transformed.

In addition, the vectors preferably contain a marker to provide a phenotypic trait for selection of transformed host cells such as dihydrofolate reductase or metallothionein. Additionally a replicating vector might contain a replicon.

Illustrative of cell cultures useful for the production of proteins are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, COS-7 or MDCK cell lines.

As indicated above, the vector which is used to transform the host cell preferably contains gene sequences to initiate the transcription and translation of the protein's gene sequence. These sequences are referred to as expression control sequences. When the host cell is of mammalian or insect origin illustrative useful expression control sequences are obtained from the SV-40 promoter, Science, 222, 524-527 (1983), the CMV I. E. promoter, Proc. Natl. Acad. Sci. 81:659-663 (1984) the metallothionein promoter, Nature, 296, 39-42, (1982) or the baculovirus polyhedrin promoter (insect cells), Virol., 131, 561-565 (1983). The plasmid or replicating or integrating DNA material containing the expression control sequences is cleaved using restriction enzymes and adjusted in size as necessary or desirable and ligated with cDNA coding for proteins by means well known in the art.

As with yeast when higher animal host cells are employed, polyadenylation or transcription terminator sequences from known mammalian genes need to be incorporated into the vector. An example of a terminator sequence is the polyadenylation sequence from the bovine growth hormone gene.

Additionally gene sequences to control replication in the host cell may be incorporated into the vector such as those found in bovine papillomavirus type-vectors, Saveria-Campo, "Bovine papillomavirus DNA: a eukaryotic cloning vector", DNA cloning Vol. II—A practical approach, Glover, ed., IRL Press, Arlington, Va. 213-238 (1985).

The preferred expression vector useful for expressing proteins in Chinese hamster ovary (CHO) cells is a shuttle vector pSVCOW7 which replicates in both CHO and *E. coli* cells utilizing ampicillin resistance and dihydrofolate reductase genes as markers in *E. coli* and CHO cells respectively. Plasmid pSVCOW7 also provides the polyadenylation sequence from bovine growth hormone which is necessary for expression in CHO cells. Plasmid pSVCOW7 is cleaved and a viral promoter and cDNAs inserted.

The preferred expression vector useful in forming recombinant baculovirus for expressing proteins in insect cells is pAc373, Smith, et al., Mol. Cell. Biol. 3:2156-2165 (1983). The plasmid replicates in *E. coli* cells utilizing ampicillin resistance, and provides the eukaryotic promoter and polyadenylation signal from the baculovirus polyhedrin gene for expression of genes. Plasmid pAc373 is cleaved and a cDNA is inserted adjacent to the promoter. This new plasmid is cotransfected with baculovirus (Autograpa californica nuclear polyhedrosis virus) DNA into insect cells by calcium phosphate precipitation. Recombinant baculovirus in which the pAc373 polyhedrin gene containing a cDNA has replaced the resident viral polyhedrin gene by homologous recombination is detected by dot blot hybridization using $^{32}P$-labeled cDNA as a probe, Summers and Smith, A Manual of Methods for Baculovirus Vectors and Insect Cell Culture Procedures, Texas A & M University, College Station, TX, 29-30 (1986). Insect cells infected with recombinant baculovirus may also be differentiated by their occlusion-negative morphology since the insertion of the cDNA into the polyhedrin gene prevents the synthesis of this occlusion-forming protein.

The preferred expression vector used in conjunction with bovine papilloma virus (BPV) for expressing proteins is pTFW9 (Plasmid pTWF9 was deposited in accordance with the Budapest Treaty. Plasmid pTFW9 is maintained in an *E. coli* host and has been deposited with the Northern Regional Research Center, Peoria, Ill., USA on Nov. 17, 1986 and assigned Accession Number NRRL B-18141.) The plasmid replicates in *E.*

*coli* utilizing ampicillin resistance, and provides the mouse metallothionein promoter and SV40 polyadenylation signal for expression of genes. Plasmid pTFW9 is cleaved and a cDNA is inserted adjacent to the promoter. This new plasmid is then cleaved to allow insertion of BPV. The recombinant plasmid is transfected into animal cells by calcium phosphate precipitation and foci of transformed cells are selected.

The host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, and microinjection of the DNA directly into the cells. The transfected cells are cultured by means well known in the art, Biochemical Methods in Cell Culture and Virology, Kuchler, Dowden, Hutchinson and Ross, Inc., (1977). Recombinant glycoproteins expressed in one of the above eukaryotic expression systems are isolated from cell suspensions created by disruption of the host cell system by well known mechanical or enzymatic means. Proteins which are designed to be secreted from the cells are isolated from the media without disruption of the cells. For purification of glycoproteins it is helpful to first apply the cytoplasmic fraction to a lentil lectin column which will specifically bind glycoproteins. The eluted glycoproteins are then applied to an affinity column containing antibody.

A typical glycoprotein can be divided into three regions. At the amino terminal end is a hydrophobic region called the signal sequence. This sequence of amino acids signals the transport of the glycoprotein to the cell membrane. Following transport the signal sequence is removed by cleavage. Downstream from the signal sequence is the extracellular domain of the mature glycoprotein. This is the immunogenic portion of the glycoprotein since it is accessible to antibodies. At the carboxy terminal end of the glycoprotein is the hydrophobic anchor region which causes the glycoprotein to be retained in the cell membrane. The HRSV F is a typical glycoprotein in that it contains an amino terminal signal sequence and carboxy terminal anchor sequence, Collins, et al., PNAS 81:7683-7687, (1984). However, the HRSV G glycoprotein is unusual since its amino terminal end acts as both a signal and anchor region, Wertz, et al., PNAS 82:4075-4079, (1985).

A glycoprotein may be designed to be secreted from cells into the surrounding media. This is accomplished by causing the early termination of the glycoprotein before transcription of the anchor region, Lasky, et al., Biotechnology, 2:527-532 (1984). Early termination may be accomplished by inserting a universal translational terminator oligonucleotide into an appropriate site in the gene's DNA. These oligonucleotides are commercially available. Early termination may also be accomplished by altering the reading frame, thus generating a translational termination codon.

Suitably, the glycoprotein would be a polypeptide comprising at least one immunogenic fragment from both human respiratory syncytial virus glycoproteins F and G, additionally comprising a signal sequence from glycoprotein F. In order, beginning with the N terminal end, the polypeptide comprises the signal sequence from glucoprotein F, an immunogenic fragment of glycoprotein F, and an immunogenic fragment of glycoprotein G.

The chimeric glycoprotein described below consists of the signal and extracellular domains of HRSV F linked to the extracellular domain of HRSV G, and will be referred to as FG. The majority of the extracellular domain of the G glycoprotein is contained within the coding region spanned by the DdeI (nucleotide position 302) and FoKI (nucleotide position 850) restriction enzyme sites. This sequence does not code for the signal/anchor region of the glycoprotein. The majority of the extracellular domain of the F glycoprotein is contained within the coding region prior to the NsiI (nucleotide position 1479) restriction enzyme site. This sequence codes for the signal region and the majority of the antigenic region, but not the anchor region of the glycoprotein.

To insert the G glycoprotein sequence into the F glycoprotein, the plasmid G-16 containing the HRSV gpG is digested with DdeI and FoKI and the ends are made blunt with Klenow polymerase. The 550 bp fragment is then isolated by agarose gel electrophoresis. The plasmid pGPF-4 containing the HRSV gpF gene was digested with NsiI. The ends were made blunt with T4 DNA polymerase and dephosphorylated with bacterial alkaline phosphatase. The 550 bp fragment from G-16 is then ligated into the pGPF-4 plasmid and transformed into *E. coli* HB101. One of the clones, pGPFG-1, isolated from the transformation is verified as having the correct junctions by Maxim-Gilbert sequencing.

When properly placed in a eukaryotic expression vector, the FG gene described above is designed to express a chimeric glycoprotein which would be transported to the cell's surface and secreted into the media.

The above restriction enzyme sites were chosen because they allow for the expression of a large proportion of the relevant regions of the F and G glycoproteins. However, other portions of the glycoproteins could be expressed by choosing other restriction enzyme sites within the F and G coding sequences for the fusion of these genes. For instance, the restriction enzymes AluI, HincII or HinfI could be used to cleave at the 5' end of the gpG gene. The restriction enzymes HphI, MboII or XhoII could be used to cleave at the 3' end of the gpG gene. The enzymes could be used in any combination of two with one enzyme being from each group to give immunogenic protein fragments. For the gpF gene, the HinfIII, HincII, AvaII, SspI or HphI restriction enzymes could be used in place of NsiI. Linker oligonucleotides could be added to correct the reading frame in the junction regions. Two oligonucleotides which would correct the two possible frame shifts are the SalI linkers GGTCGACC and CGGTCGACCG
CCAGCTGG GCCAGCTGGC which are commercially available. Also when an anchor region is desired in the glycoprotein, a linker oligonucleotide is added at the second junction to allow synthesis of the gpF anchor region. Alternative strategies could be designed for the expression of a FG fusion protein by insertion or deletion of various sequences. The major criterion for the protein is the retention of a signal sequence and the immunologically important regions of the two glycoproteins.

Insertion of FG gene into CHO, BPV, or baculovirus expression vectors is as already described.

The FG chimeric glycoprotein offers advantages over expression of the individual glycoproteins. Since FG is a single protein, it requires half the labor and reagents for purification compared to the separate F and G glycoproteins. Also, the FG chimeric glycoprotein is secreted into the media for ease of purification. The F glycoprotein can be engineered as a secreted glycoprotein by truncation prior to the anchor region sequences. However, the HRSV G glycoprotein contains a signal/anchor region at its amino terminal end. Therefore, truncation of this glycoprotein will not generate a secreted form. The signal/anchor region could be replaced with a signal region from a foreign glycoprotein, but this would introduce foreign protein sequences into the potential vaccine.

The HRSV F and G glycoproteins have been expressed using a vaccinia virus expression system, and these recombinant viruses have been used as vaccines in the protection of cotton rats from HRSV infection, Olmsted, et al., PNAS 83:7462-7466, (1986). Vaccinia virus expressing the F glycoprotein was significantly more immunogenic and provided better protection than vaccinia virus expressing the G glycoprotein, Olmsted et al., supra. Vaccination with both viruses did not appear to have an additive effect over F alone Olmsted, et al., supra. In contrast, the secreted FG glycoprotein appears to be more immunogenic and provide better protection than a secreted form of the F glycoprotein. Also, vaccination of cotton rats with the FG protein produces a higher percentage of neutralizing antibody as defined by the ELISA to neutralization ratio.

An experiment was designed to compare the immunogenicity of FG and truncated F (Ft). Because the recombinant glycoproteins could not be detected in ConA (a lectin which binds glycoproteins) purified extracts by Commassie blue staining of proteins electrophoresed in SDS-PAGE gels (probably less than 1% of the protein), an indirect method was used to determine equivalent amounts of the glycoproteins. Densitometer tracings of autoradiograms containing $^{35}$S-methionine labeled protein which had been electrophoresed on a SDS-PAGE gel was used to determine the relative amount of FG and Ft in the samples (FG and Ft contain the same number of methionines). These same samples were then assayed by ELISA, and it was determined that equivalent amounts of FG react 3 times better than Ft in our ELISA assay. The amount of FG or Ft in the samples prepared for vaccination was then determined by ELISA and equalized according to the above ratio. The groups in the study were FG, Ft (high dose), Ft (low dose), and gp50 (neg. control). The cotton rats are vaccinated three times in Freund's adjuvant, 500 μg total protein per dose. The amount of specific glycoprotein in the FG group is equivalent to the low dose Ft group. The high dose Ft group received 3 times more specific glycoprotein. A summary of the data from this study is presented below.

| GROUP | LUNG TITER (pfu/gm lung) | ELISA TITER (50% end pt) | NEUT. TITER (50% end pt) | ELISA/NEUT. Ratio |
|---|---|---|---|---|
| FG | <55 | 1300 | 850 | 1.53 |
| Ft high | $2.0 \times 10^2$ | 1400 | 285 | 4.91 |
| Ft low | $6.1 \times 10^3$ | 1000 | 206 | 4.85 |
| gp50 | $2.7 \times 10^5$ | <100 | 40 | ND |

The above study demonstrates the efficacy of the chimeric FG glycoprotein using crude preparations of FG in Freund's adjuvant. To demonstrate the efficacy of FG to induce high titers of neutralizing antibody and protect cotton rats from RSV challenge, a study was undertaken using more purified preparations of FG formulated in an adjuvant acceptable for human use (alum). FG was purified to 50% homogeneity using a two step procedure involving cation exchange and monoclonal antibody affinity columns. The Ft glycoprotein was purified to 50% homogeneity by lentil lectin chromatography followed by monoclonal antibody affinity chromatography. Cotton rats were vaccinated twice with these glycoproteins adsorbed in alum (2.5 mg alum/dose). One group of rats was vaccinated intranasally with live RSV as a positive control. One group of rats was vaccinated with the alum adjuvant as a negative control. Rats from each group were tested for serum and neutralizing antibody. The rats were challenged with RSV and the lungs were assayed for virus.

| Group | Serum Ab | Neut. Ab | # Infected/ Total | Avg. Lung Titer of Infected Rats |
|---|---|---|---|---|
| 25 μg FG + Alum | 19500 | 2834 | 0/7 | — |
| 5 μg FG + Alum | 19200 | 2027 | 0/6 | — |
| 1 μg FG + Alum | 12000 | 4096 | 3/7 | $3.5 \times 10^2$ |
| 25 μg FG + CFA | 21500 | 5029 | 1/7 | $1.0 \times 10^2$ |
| 25 μg FT + Alum | 13500 | 263 | 2/7 | $3.0 \times 10^2$ |
| 5 μg FT + Alum | 13000 | 194 | 4/7 | $6.7 \times 10^2$ |
| Alum Cont. | <500 | 10 | 7/7 | $9.7 \times 10^4$ |
| RSV I.N. | 7100 | 217 | 1/7 | 50 |

Conventions used to represent plasmids and fragments in Charts 1-6, are meant to be synonymous with conventional circular representations of plasmids and their fragments. Unlike the circular figures, the single line figures on the charts represent both circular and linear double-stranded DNA with initiation or transcription occurring from left to right (5' to 3'). Asterisks (*) represent the bridging of nucleotides to complete the circular form of the plasmids. Fragments do not have asterisk marks because they are linear pieces of double-stranded DNA. Endonuclease restriction sites are indicated above the line. Gene markers are indicated below the line. Bars appearing below the diagrams representing the plasmid or fragments are used to indicate the number of basepairs between two points on the DNA. The relative spacing between markers do not indicate actual distances but are only meant to indicate their relative positions on the illustrated DNA sequence.

EXAMPLES

EXAMPLE 1

Removing the G-C tails from the F glycoprotein gene

In order to obtain maximum expression of the F glycoprotein, the G-C nucleotides which are used to insert the cDNA into the plasmid pBR322 must be removed from the 5' end (relative to the original mRNA) of the cDNA. In order to conveniently insert the gpFG cDNA into the preferred expression vector for CHO cells, pSVCOW7 (described below), it is necessary to supply a BamHI site upstream from the protein coding sequence. To accomplish this the cDNA of F glycoprotein is inserted into pUC12 (PL Pharmacia Labs, Piscataway, N.J.). Methods for the synthesis of the cDNA clone F5-25 containing the entire sequence for the F glycoprotein has been described. Collins, et al., Nucleotide sequence of the gene encoding the fusion (F) glycoprotein of human respiratory syncytial virus, J. Virol., 81:7683-7687 (December 1984).

A. Construction of pGPF2—Chart 1

The cDNA of the F glycoprotein is flanked by PstI sites (Chart 1), however there are also internal PstI sites. Therefore, the plasmid pF5-25 is partially digested with PstI and fragment 1 (1.9 kb) is isolated from a gel. Fragment 1 is ligated to the plasmid pUC12 (Bethesda Res. Labs,, Rockville, Md.) which had been digested with PstI. A plasmid with the 5' end of the gpF gene adjacent to the XbaI site in pUC12 is selected and designated pGPF2 (4.6 kb). This orientation is verified by cleavage with NsiI and HindIII which generates a fragment of approximately 400 bp.

B. Construction of pGPF3 and pGPF4—Chart 2

To remove the G-C nucleotides from the 5' end of the cDNA, pGPF2 is opened with XbaI and the ends are treated with bacterial alkaline phosphatase to yield fragment 3. Fragment 3 is then digested with SalI which cuts off a small piece between the XbaI and PstI sites and treated with Klenow enzyme to make the ends flush. After treatment with Klenow enzyme, fragment 3 is digested with Lambda exonuclease which requires a 5' phosphate and leaves a 3' overhang. Because of the removal of the 5' phosphate on the end upstream from the gpF, the exonuclease will digest downstream toward the gpF sequence. The exonuclease is allowed sufficient time to remove nucleotides beyond the G/C tail region into the leader sequence. A synthetic sequence containing the first 15 bases of the leader sequence is hybridized to fragment 3 and the missing bases filled in with Klenow enzyme and the ends ligated with T4 ligase to yield pGPF3 (4.6 kb) which is transformed into *E. coli* and its sequence verified.

To remove the G-C nucleotides from the 3' end of the cDNA, pGPF3 is opened with HindIII and treated with the exonuclease Bal 31 for a time sufficient to digest through the G-C nucleotides. The ends are made blunt with Klenow enzyme and the cDNA clone is freed from the vector DNA by digestion with BamHI. The cDNA fragment is isolated from a gel and ligated to plasmid pUC12 which has been digested with BamHI and HincII (HincII is compatible with blunt ends) to yield pGPF4. The plasmid is transformed into *E. coli* and an appropriate clone which was sufficiently digested with Bal31 is identified by sequencing. Alternatively, the G-C nucleotides may be removed by digesting with a restriction enzyme which has a unique site upstream from the G-C nucleotides. For gpF such an enzyme would be HaeIII. Since HaeIII cleaves upstream from the F gene's normal translation termination signal, a universal translation termination oligonucleotide (New England Biolabs) would be ligated onto the F cDNA after digestion with HaeIII. The DNA would then be digested with BamHI and treated as described above for generating pGPF-4.

EXAMPLE 2

Construction of a HRSV Chimeric FG Glycoprotein Gene—Chart 3

A. Preparation of the HRSV G glycoprotein gene

Clone G2B-16 containing the entire coding region for the HRSV G glycoprotein has been described (Wertz, et al., Nucleotide sequence of the G protein gene of human respiratory syncytial virus reveals an unusual type of viral membrane protein, PNAS, 82:4075-4079 (1985)). Clone G2B-16 containing the G glycoprotein cDNA is digested with DdeI and FoKI and the ends are made blunt with *E. coli* DNA polymerase (Klenow fragment). The DNA is then electrophoresed in a 1.5% agarose gel. The 550 bp fragment (fragment 4) containing the relevant region of the G gene is excised from the gel and the DNA is purified from the agarose.

B. Insertion of the G cDNA fragment into the HRSV F glycoprotein gene

The plasmid pGPF4 (Chart 2) is digested with NsiI. The ends are made blunt with T4 DNA polymerase and then dephosphorylated with bacterial alkaline phosphatase. The 550 bp fragment of the G cDNA is then ligated into plasmid pGPF4 to yield the chimeric FG gene (pGPFG-1). The plasmid is transformed into *E. coli* HB101. Clones are isolated and selected for the correct orientation of the G cDNA within the F gene by digestion with HinfI which will generate junction fragments of 875 bp and 186 bp. The incorrect orientation of the G fragment will yield junction fragments of 650 bp and 400 bp upon HinfI digestion. The junction regions of a properly orientated clone are then verified as correct by Maxam-Gilbert sequencing.

The above example will generate a gene coding for a chimeric glycoprotein containing the signal and immunogenic region of the F glycoprotein linked to the immunogenic region of the G glycoprotein. Since the second junction (G to F) causes a frame shift and translational termination, no anchor region will be present in the glycoprotein.

EXAMPLE 3

Using DNA Oligonucleotide Linkers to Adjust the Reading Frame of a HRSV Chimeric FG Glycoprotein—Chart 4

If restriction enzymes other than those presented in example 2 are used for linking the F and G genes, a frame shift may occur at the first junction between F and G leading to early translational termination of the glycoprotein. This can be overcome by using oligonucleotide linkers which will restore the correct reading frame.

A. Preparation of the HRSV G glycoprotein gene

Clone plasmid G2B-16 containing the G glycoprotein cDNA is digested with HphI and the ends are made blunt with T4 DNA polymerase. The SalI linker

CGGTCGACCG
GCCAGCTGGC (New England Biolabs) is ligated to the ends of the DNA. The DNA is digested with SalI and electrophoresed in a 1.5% agarose gel. The 410 bp fragment (fragment 5) containing the relevant region of the G gene is excised from the gel and the DNA is purified from the agarose.

B. Insertion of the G cDNA fragment into the HRSV F glycoprotein gene

The plasmid pGPF4 is digested with NsiI and the ends are made blunt with T4 DNA polymerase. The SalI linker indicated above is ligated to the ends of the pGPF4 DNA. The DNA is digested with SalI and electrophoresed in a 1% agarose gel. The 4.4 kb fragment is excised from the gel and the DNA is purified from the agarose. The 4.4 kb pGPF4 DNA fragment and the 410 bp G fragment are ligated together forming pGPFG-2 and transformed into *E. coli* HB101. Clones are isolated and selected for the correct orientation of the G cDNA within the F gene by digestion with HinfI which will generate junction fragments of 768 bp and 220 bp. The incorrect orientation of the G fragment will yield junction fragments of 555 bp and 430 bp upon HinfI digestion. The junction regions of this clone are then verified as correct by Maxam-Gilbert sequencing.

The above example will generate a gene coding for a chimeric FG glycoprotein similar to that in Example 2. The chimeric glycoprotein generated in this example would contain less of the immunogenic regions of the G glycoprotein than the chimeric generated in Example 2. Chimeric glycoproteins containing other regions of the two glycoproteins can be generated as described in Examples 2 and 3 using the enzymes listed in the "Detailed Description" section.

EXAMPLE 4

Using DNA Oligonucleotides to Generate Genes Coding for Chimeric FG Glycoproteins of Various Lengths—Chart 5

Genes coding for chimeric FG glycoproteins containing various regions of the F and G glycoproteins can be generated using a combination of restriction enzymes and oligonucleotides. This procedure allows the F and G glycoproteins to be linked at any desirable point on their amino acid backbone, permitting incorporation or removal of regions likely to contain epitopes which will be recognized by the host immune system. Individual amino acids may also be changed if so desired. Oligonucleotides are synthesized corresponding to the DNA sequence from the point of desired linkage to a convenient restriction enzyme site. The glycoprotein gene is digested with that restriction enzyme and the oligonucleotide is ligated to the gene at the restriction enzyme site to generate a DNA fragment of the desired length. The oligonucleotides are synthesized with ends compatible with the restriction enzyme sites for easy ligation.

A. Preparation of HRSV F glycoprotein gene

The plasmid pGPF4 is digested with NsiI and ligated to either oligonucleotide 1 (cDNA nucleotides 1483–1519) or a mixture of oligonucleotides 1 and 2. Oligonucleotides 1 and 2 (cDNA nucleotides 1483–1564) would extend the glycoprotein F DNA incorporated into the chimeric gene to the DNA sequences just prior to the anchor-encoding region of the F glycoprotein. The DNA sequences in these 2 oligonucleotides may code for additional epitopes found on the F glycoprotein. Parentheses surround the nucleotides on the 3′ end of oligonucleotide 1 which would be included if it were to be the terminal oligonucleotide. The indicated nucleotides code for a HindIII restriction enzyme site. If oligonucleotide 2 is also to be included, then the indicated nucleotides on oligonucleotide 1 are excluded to allow ligation of the 3′ end of oligonucleotide 1 with the 5′ end of oligonucleotide 2. The 3′ end of oligonucleotide 2 also contains a HindIII site.

Following ligation of the oligonucleotide(s), the DNA is digested with HindIII (HindIII sites in oligonucleotide at 3′ end of the F gene and in the polylinker region of pUC12 plasmid) and the plasmid is religated. The DNA is transformed into *E. coli* HB101 and a clone containing the oligonucleotide(s) linked to the F gene is isolated (pGPF5). The presence of the oligonucleotide(s) in the clone can be verified by hybridization of the clone with $^{32}P$-labeled oligonucleotide(s).

B: Insertion of glycoprotein G cDNA into the F glycoprotein gene

Clone G2B-16 is digested with HinfI and XhoII. The 277 bp fragment representing the cDNA region from nucleotide position 377 to 654 is gel purified. Oligonucleotides representing adjoining regions of the G cDNA are then ligated to each end of the G fragment. The DNA sequences in these oligonucleotides may code for additional epitopes found on the G glycoprotein. The individual oligonucleotides were designed to incorporate regions which may contain unique epitopes. The oligonucleotide ligated to the 5′ end of the G cDNA may consist of either oligonucleotide 3 (cDNA nucleotides 297–377) or oligonucleotide 3 linked to oligonucleotide 4 (cDNA nucleotides 213–377). The oligonucleotide ligated to the 3′ end of the G cDNA may consist of oligonucleotide 5 (cDNA nucleotides 654–714), oligonucleotides 5-6 (cDNA nucleotides 654–774), oligonucleotides 5-6-7 (cDNA nucleotides 654–843), or oligonucleotides 5-6-7-8 (cDNA nucleotides 654–912). Parentheses enclose nucleotides which would be included only in the terminal oligonucleotide. For instance, the enclosed nucleotides would not be included on oligonucleotide 5 if oligonucleotide 6 were to be added. These enclosed nucleotides code for a HindIII site and in the case of oligonucleotides 5, 6, 7, and 8 a translational termination codon. The enclosed nucleotides are not included when an additional oligonucleotide(s) is to be added in order to allow ligation between the compatible ends of the oligonucleotides. For instance, the 5′ end of oligonucleotide 3 is compatible with the 3′ end of oligonucleotide 4 when the nucleotides enclosed by parentheses are not included in oligonucleotide 3.

Following ligation of the oligonucleotides to the G cDNA fragment, the DNA is digested with HindIII and the enlarged G cDNA fragment (fragment 7) is gel purified. The new G cDNA fragment is then ligated to the F clone prepared in section A of this example (pGPF-5) which has been digested with HindIII. The DNA is transformed into *E. coli* HB101 and a clone containing the G gene in the correct orientation within the F gene is isolated (pGPFG-3). Orientation is determined by digestion with appropriate restriction enzymes. The newly synthesized regions of the chimeric gene are verified correct by Maxam-Gilbert sequencing. The clone may then be placed in various expression vectors as described below.

C. Oligonucleotides

```
1)      TCAATATCTCAAGTCAACGAGAAGATTAACCAGAGC(CTAGCA AAGCTT)
   ACGTAGTTATAGAGTTCAGTTGCTCTTCTAATTGGTCTCG GATCGT(TTCGAA)

2) CTAGCATTTATTCGTAAATCCGATGAATTATTACATAATGTAAATGCTGGTAAATCCAAGCTT
           AAATAAGCATTTAGGCTACTTAATAATGTATTACATTTACGACCATTTAGGTTCGAA
```

-continued

C. Oligonucleotides 3) (AAGCTT) CCTCAG CTTGGAATCAGTCCCTCTAATCCGTCTGAAATTACATCACAATCACCA
(TTCGAA GGAGTC) GAACCTTAGTCAGGGAGATTAGGCAGACTTTAATGTAGTGTTAGTGGT

CCATACTAGCTTCAACAACACCAGG
GGTATGATCGAAGTTGTTGTGGTCCTCA

4) AAGCTTCACAAAGTCACACCAACAACTGCAATCATACAAGATGCAACAAGCCAGATCAAGA
TTCGAAGTGTTTCAGTGTGGTTGTTGACGTTAGTATGTTCTACGTTGTTCGGTCTAGTTCT

ACACAACCCCAACATACCTCACCCAGAAT
TGTGTTGGGGTTGTATGGAGTGGGTCTTAGGAGTC

5) GATCCCAAACCTCAAACCACTAAATCAAAGGAAGTACCCACCACCAAGCCCACA(GAAGAG
GGTTTGGAGTTTGGTGATTTAGTTTCCTTCATGGGTGGTGGTTCGGGTGT CTTCTC

TAGAAGCTT)
(ATCTTCGAA)

6) GAAGAGCCAACCATCAACACCACCAAAACAAACATCATAACTACACTACTCACCTCCAAC
GGTTGGTAGTTGTGGTGGTTTTGTTTGTAGTATTGATGTGATGAGTGGAGGTTG (ACCACA(TAGAAGCTT)
TGGTGT(ATCTTCGAA)

7) ACCACAGGAAATCCAGAACTCACAAGTCAAATGGAAACCTTCCACTCAACTTCCTCCGAA
CCTTTAGGTCTTGAGTGTTCAGTTTACCTTTGGAAGGTGAGTTGAAGGAGGCTT

GGCAATCCA(AGCCCT TAGAAGCTT)
CCGTTAGGT TCGGGA(ATCTTCGAA)

8) AGCCCTTCTCAAGTCTCTACAACATCCGAGTACCCATCACAACCTTCATCTCCACCCAACA
AGAGTTCAGAGATGTTGTAGGCTCATGGGTAGTGTTGGAAGTAGAGGTGGGTTGT

CACCACGCCAGTAGAAGCTT
GTGGTGCGGTCATCTTCGAA

EXAMPLE 5

Construction of a HRSV Chimeric FG Glycoprotein Gene Containing an Anchor Region—Chart 6

Examples 2, 3, and 4 illustrate the synthesis of genes coding for chimeric FG glycoproteins which do not contain anchor regions and will therefore be secreted into the medium of expressing cells. A gene coding for a chimeric FG glycoprotein containing an anchor region can be synthesized. The anchor region would cause the retention of the chimeric glycoprotein in the cellular membranes in a manner similar to most viral glycoproteins. The anchor region may be on the carboxy-terminal end of the glycoprotein so that the immunogenic regions of the chimeric molecule from both the F and G glycoproteins would protrude into the extracellular fluid. The gene described below will code for a chimeric glycoprotein consisting of the extracellular region of HRSV F, the extracellular region of HRSV G, and the anchor region of HRSV F in the above order from amino-terminus to carboxy-terminus.

A. Insertion of the G cDNA fragment into the HRSV F glycoprotein gene

The clone G2B-16 is digested with DdeI and FoKI. The following oligonucleotides are then ligated to the ends of the DNA fragment:

9) ATGCATCACC
TACGTAGTGGAGT

10) CAAGTCGATGCAT
AGCTACGTA

Following ligation, the DNA is digested with NsiI and the 550 bp fragment of the G cDNA (fragment 8) is gel purified. The 550 bp fragment is then ligated into NsiI digested pGPF4. The DNA is transformed into *E. coli* HB101. Clones are isolated and selected for the correct orientation as described in Example 2. The junction regions of a properly orientated clone are then verified correct by Maxam-Gilbert sequencing. This clone (pGPFG-4) may be placed in various expression vectors as described below.

EXAMPLE 6

Construction of a HRSV Chimeric GF Glycoprotein Gene

A portion of the extracellular region of the HRSV F glycoprotein may be placed at the carboxy-terminal end of the G glycoprotein. This chimeric glycoprotein would consist of the signal/anchor region from the amino-terminus of G, the majority of the extracellular region of G, and a portion of the extracellular region of F in the above order from amino-terminus to carboxy-terminus.

A. Preparation of the HRSV G glycoprotein gene—Chart 7

To prepare clone G2B-16 for expression, the G-C tails used in cDNA cloning must be removed and compatible restriction enzyme sites placed on its ends. Clone G2B-16 is digested with NlaIII and FoKI. NlaIII cleaves at position 18 and FoKI at position 846 on the cDNA gene sequence. The following oligonucleotides are then ligated to the cDNA fragment:

11) GATCCAAATGCAAACATG
GTTTACGTTT

-continued

12) CAAGTCTCTCTACAG
AGAGAGATGTCAGCT

Oligonucleotide 11 will ligate to the NlaIII site and generate a BamHI restriction enzyme site on the 5' end of the cDNA fragment. Oligonucleotide 12 will ligate to the FoKI site and generate a SalI restriction enzyme site on the 3' end of the cDNA fragment. The DNA is electrophoresed in a 1.5% agarose gel. The 850 bp G cDNA fragment (fragment 9) is excised from the gel and the DNA is purified from the agarose. The G cDNA fragment is then ligated into pUC12 which has been digested with BamHI and SalI to yield pGPG-1. The plasmid is transformed into *E. coli* HB101 and plasmid DNA is isolated.

B. Insertion of an F cDNA fragment into the HRSV G glycoprotein gene—Chart 8

The clone F5-25 is digested with XhoII and NsiI. XhoII cleaves at position 446 and NsiI at position 1483 on the F cDNA gene sequence. The following oligonucleotides are then ligated to the cDNA fragment.

13) TCGACGGTGGTG
GCCACCACCTAG

14) TCAATATCTTAG
ACGTAGTTATAGAATCAGCT

Oligonucleotide 13 will ligate to the XhoII site and will generate a SalI restriction enzyme site on the 5' end of the cDNA fragment. Oligonucleotide 14 will ligate to the NsiI site and will generate a SalI restriction enzyme site and a translational termination codon on the 3' end of the cDNA fragment. The DNA is then digested with SalI, and the 960 bp F cDNA fragment (fragment 10) is gel purified. The F cDNA fragment is then ligated into pGPG-1 which has been digested with SalI. The plasmid is transformed into *E. coli* HB101. Clones are isolated and selected for the correct orientation of the F cDNA within the G gene by digestion with BamHI and NsiI which will generate a 1.8 kb fragment. The incorrect orientation will generate a 850 bp fragment. The junction regions of a properly orientated clone are then verified correct by Maxam-Gilbert sequencing. This clone (PGPGF-1) may be placed in various expression vectors as described below.

EXAMPLE 7

Expression of the Chimeric FG Glycoprotein of HRSV in CHO Cells

A. Construction of pSVCOW7

The starting plasmid pSV2dhfr (available from the American Type Culture Collection or prepared according to the procedure of S. Subramani, et al., "Expression of the Mouse Dihydrofolate Reductase Complementary Deoxyribonucleic Acid in Simian Virus 40", Molecular and Cellular Biology 2:854–864 (September 1981) is digested with BamHI and EcoRI to yield a 5.0 kb fragment containing the ampicillin resistance gene, the SV40 origin, and the dhfr gene. The second portion of pSVCOW7 is obtained from plasmid pλGH2R2 which is digested with the same restriction endonucleases used to cleave pSV2dhfr to obtain a 2.1 kb fragment containing the 3' end of genomic bovine growth hormone gene, i.e., BGH gDNA. Plasmid pλGH2R2 is publicly available from an *E. coli* HB101 host, deposited with the Northern Regional Research Laboratories in Peoria, Ill. (NRRL B-15154). The 5.0 kb and 2.1 kb fragments are ligated to yield pSVCOW7 (7.1 kb).

B. Construction of pGPFG-IE-PA

The genes constructed in Examples 2–6 may be used for expression of a chimeric glycoprotein in CHO cells. The plasmid pGPFG-1 will be used in the following example. The other chimeric genes are treated as described for pGPFG-1 except when otherwise indicated. The assembly of pGPFG-IE-PA is accomplished in two steps. First the gpFG cDNA from pGPFG1 is inserted into pSVCOW7 yielding pGPFG-PA and then the immediate early promoter of cytomegalovirus is inserted to initiate transcription of the HRSV-like proteins yielding pGPFG-IEPA.

STEP 1. Plasmid pSVCOW7 is cut with EcoRI and PvuII and fragment 11 (600 bp) containing the polyadenylation sequence of bovine growth hormone extending from the PvuII site in the 3' most exon of the BGH gene, to the EcoRI site downstream from the 3' end is isolated. For a complete discussion of the BGH polyadenylation sequence see the following references: (1) European patent application 0112012, published on Jun. 27, 1984 wherein the identification and characterization of BGH genomic DNA is disclosed; (2) Woychik, R. P. et al., "Requirement for the 3' Flanking Region of the Bovine Growth Hormone Gene for Accurate Polyadenylation", Proc. Natl. Acad. Sci. USA 81:39444–3948 (July 1984); and, D. R. Higgs, et al., Nature 306:398–400 (Nov. 24, 1983) and references cited therein disclosing that the nucleotide sequence AATAAA characterizes the polyadenylation signal at a location 11 to 30 nucleotides upstream (towards the 5' end) from the 3' end of the BGH gene.

A second sample of pSVCOW7 is cut with EcoRI and BamHI to yield fragment 12 (5.8 kb). Fragment 12 can be alternatively derived from the EcoRI/BamHI fragment from parent plasmid pSV2dhfr available from Bethesda Research Laboratories. Fragment 12 contains the orgin of replication from pBR322 and an ampicillin resistance gene expressed in *E. coli* which allows for the selection of the plasmid in *E. coli.* The fragment also contains the mouse dihydrofolate reductase cDNA in a construction that allows expression in mammalian cells. Subramani, et al., Mol. Cell. Biol. 1:854–864 (1981).

Plasmid pGPFG1 is cut with HindIII (pGPFG-3 is digested with HpaI), treated with Klenow enzyme and recut with BamHI to yield fragment 13 (2.2 kb) which is gel isolated. The BamHI site is just upstream from the cDNA coding for the 5' untranslated sequences of the FG mRNA, and the HindIII site is in pUC12 vector a few bases pairs beyond the PstI site near the 3' end of the gpFG cDNA (HpaII site in pGPFG-3 is 95 bp from 3' end of FG cDNA).

Fragments 11, 12 and 13 are ligated to form pGPFG-PA (8.6 kb) which is a replication vector capable of shuttling between *E coli* and CHO cells. Plasmid pGPFG-PA is transformed into *E coli.*

STEP 2. In step 2, pGPFG-PA is converted into expression plasmid pGPFG-IE-PA by inserting the immediate early gene promoter from human cytomegalovirus (CMV I.E. promoter). The CMV I.E. promoter is obtained from the PstI digestion of the CMV genome. The restriction endonuclease cleavage maps of the region of the human cytomegalovirus (CMV) genome containing the major immediate early gene (CMV I.E.) have been described in detail Stinski, et al., J. Virol. 46:1-14, 1983; Stenberg, et al., J. Virol. 49:190-199, 1984; and, Thomsen, et al., Proc. Natl. Acad. Sci. USA, 81:659-663, 1984.

The Stinski and Thomsen references describe a 2.0 kilobase PstI fragment which contains the promoter for the major immediate early gene. When this 2.0 kb PstI fragment is isolated and digested with Sau3AI, a 760 basepair fragment is obtained among the products. This 760 base pair fragment can be distinguished from the other products by its size and the presence of a SacI cleavage site and a BalI cleavage site within the fragment. Because of its convenient identification, utilization of this Sau3AI fragment is the preferred method of use of the CMV I.E. promoter as described in the present specification.

Plasmid pGPFG-PA is cleaved with BamHI, and a Sau3AI fragment containing the CMV immediate early promoter is ligated into the compatible BamHI site. Plasmids containing the CMV promoter fragment in an orientation such that transcription from the promoter would synthesize an mRNA for an HRSV-like protein are identified by cleavage of the plasmids with SacI. The resulting plasmid is designated pGPFG-IE-PA having the CMV I.E. promoter at the 5'-end of the cDNA and the BGH polyadenylation signal on its 3'-end. The plasmid is maintained in *E. coli* until transfection into CHO cells.

C. Transfection and Culturing of CHO Cells

Plasmid pGPFG-IE-PA is transfected into Chinese hamster ovary (CHO) cells deficient in dihydrofolate reductase(dhfr) using the calcium phosphate method for transfection of DNA into cells which is described in detail by Graham, et al., Introduction of Macromolecules into Viable Mammalian Cells, Alan R. Liss Inc., N.Y., 1980, pp. 3-25. The cell line used is the mutant DXB-11 originally available from L. Chasin, of Columbia University and completely described in Proc. Natl. Acad. Sci. USA 77:4216-4220 (1980). The above methods for transfection relies on the fact that cells which incorporate the transfected plasmids are no longer dhfr deficient and will grow in Dulbecco's modified Eagle's medium plus proline.

If the chimeric glycoprotein does not contain an anchor region, then supernatant from CHO cells expressing secreted chimeric FG protein is clarified by low speed centrifugation. The supernatant is applied to a conconavalin A (or lentil lectin) column. The glycoprotein is eluted after extensive washing with a linear gradient of α-D-methylglucoside (0-0.5M) in the above buffer. The eluted glycoprotein is dialyzed against PBS containing 0.1% Triton X-100 and applied to an affinity column. The affinity column is composed of either polyclonal or monoclonal antibodies directed against HRSV linked to Sepharose 4B beads (Pharmacia, Piscataway, New Jersey) by known techniques. The column is washed in dialysis buffer and the HRSV FG glycoprotein is eluted with PBS containing 0.1M glycine (pH 2.5) and 0.1% Triton X-100. The glycoprotein is dialyzed against saline and checked for purity by electrophoresis on a SDS-PAGE gel.

If the chimeric glycoprotein contains an anchor region, then the CHO cells expressing the glycoprotein are washed in phosphate buffered saline (PBS) and then lysed in PBS containing 1.0% Triton X-100 and 1.0% sodium deoxycholate. After pelleting the nuclei, the cytoplasmic extract is applied to a conconavalin A column and purified as described above for secreted glycoproteins.

EXAMPLE 8

The Expression of HRSV GPFG Using Bovine Papilloma Virus (BPV)

A. The construction of a cloning vector containing a nontranscribable expression cassette suitable for replication in *E. coli*

The constructions of pTFW8 and pTFW9 offer a convenient starting material for expressing HRSV proteins using BPV. The transcription terminator of the deposited plasmid prevents the expression of HRSV proteins and must be removed in a single step excision and ligation.

1. Construction of PTFW8

Plasmid pdBPV-MMTneo (342-12) described in Mol. and Cell Biol., Vol 3 (No. 11):2110-2115 (1983) and obtained from Peter Howley of the National Cancer Institute, Bethesda, Maryland, USA. Plasmid pdBPV-MMT neo (342-12) consists of three parts: a complete BPV-1 genome (100%) opened at the unique BamHI site; pML2 (a "poison-minus" derivative of pBR322); and a transcriptional cassette composed of the murine metallothionein I gene promoter, the neomycin phosphotransferase II gene of Tn5, and the simian virus 40 early-region transcriptional processing signals. Plasmid pdBPV-MMT neo (342-12) is first digested with BamHI to remove the BPV sequences which were isolated and stored for later insertion. The remaining fragment is religated using T4 ligase to form pMMpro.nptII (6.7 kb). Removal of the BPV genome facilitates later genetic manipulations by creating unique restriction sites in the remaining plasmid. After the recombinations are complete, the BPV genome is replaced.

Plasmid pMMpro.nptII is digested with BglII and a synthetic DNA fragment 14 containing unique restriction sites is inserted and ligated using T4 ligase to yield pTFW8 (6.7 kb). Plasmid pTFW8 is identical to pMMpro.nptII except for the insertion of unique restriction sites between the murine metallothionein I gene promoter and the neomycin resistance gene.

2. Construction of pTWF9

Plasmid pTWF9 contains the transcription terminator $T_l$ from phage lambda inserted between the metallothionein I gene promoter and the neomycin resistance gene. The transcription terminator can be obtained from Donald Court of the National Cancer Institute in Bethesda, Maryland USA. The transcription terminator is supplied in pKG1800sib3 which is the same as pUS6 as described in Gene, 28:343-350 (1984), except that $t_l$ carries the sib3 mutation as described in Guarneros et al., PNAS, 79:238-242 (1982). During the normal infection process of phage lambda, the $t_l$ terminator functions in the inhibition of bacteriophage λ int gene expression from $P_L$ and in the termination of int gene transcription originating from $P_l$. The terminator is excised from pKG800sib3 using AluI and PvuI as fragment 15 (1.2 kb), which is gel isolated and XhoI linkers are placed on either end of the fragment. The linkers are available from New England Biolabs, Beverly, MA, USA. The terminator fragment bounded by XhoI complementary ends is then inserted into pTWF8 which has been previously digested with XhoI. The fragments are then ligated using T4 DNA ligase to yield pTWF9 (7.9 kb). Plasmid pTWF9 was desposted in accordance with the Budapest Treaty. Plasmid pTFW9 is maintained in an *E. coli* host and has been deposited with the Northern Regional Research Center, Peoria, Illinois, USA on Nov. 17, 1986 and assigned Accession Number NRRL B-18141.

B. The construction of pTFW/GPFG

The genes constructed in Examples 2–6 may be used for expression of a chimeric glycoprotein using BPV. The plasmid pGPFG-1 will be used in this example. The other chimeric genes are treated as described for pGPFG-1 except when otherwise indicated. To construct pTFW/GPFG, pGPFG1 is digested with BamHI and HindIII (pGPFG-3 is digested with BamHI and HpaII). Its ends are made flush with Klenow enzyme and synthetic BglII linkers (New England Biolabs) are ligated to the ends of the clone. The DNA is digested with BglII and designated fragment 16 (2.2 kb). Fragment 16 containing the gpFG gene (2.2 Kb) is then isolated from a gel. The purified fragment is ligated into pTFW9 which has been digested with BglII to yield pTFW/GPFG (10.1 kb).

C. Conversion of pTFW/GPFG into a eukaryote expression vector

Plasmid pTFW/GPFG is converted into a eukaryote expression vector by reinserting the 100% complete BPV-1 genome excised with BamHI in step a., of Example 8A. Plasmid pTFW/GPFG is cut with BamHI and the BPV-1 intact genome, a 7.9 kb fragment is inserted to yield pTFW/GPFG/BPV* (18.0 kb) which is replicated in E. coli until production of glycoprotein FG by eukaryotic cells is desired.

D. Expression of gpFG in murine C127 cells

Prior to transfection into murine C127 cells, pTFW/GPFG/BPV* is digested with XhoI to excise the $T_I$ terminator and religated with T4 DNA ligase. The resulting plasmid pTFW/GPFG/BPV (16.9 kb) will now direct the expression of high levels of gpFG which is secreted into the culture media. The C127 cells are available from the American Type Culture Collection and grown in Dulbecco's modified minimal essential media containing 10% fetal calf serum. The levels of gpFG proteins in the media of the C127 cells are determined by Western blot experiments with anti-RSV antibody and $125_I$-labeled protein A.

HRSV gpFG is purified from the culture media or cells as described in Example 7.

EXAMPLE 9

The Expression of HRSV GPFG Using Baculovirus Virus

The following example relates to the expression of glycoprotein FG in insect cell cultures. All procedures are detailed in Summers, M.D. and Smith, G.E., A Manual for Baculovirus Vectors and Insect Cell Culture Procedures published by the College of Agriculture, Texas Agricultural Experiment Station, Texas Agricultural Extension Service, College Station, Texas, 1986. The starting plasmid pAc373 (7.1 kb) is a general baculovirus expression vector having a unique BamHI site immediately downstream from the polyhedron promoter for Autographa californica nuclear polyhedrosis virus (AcNPV). The polyhedron protein is a matrix protein that is nonessential for viral infection and replication in vitro. The plasmid is available from Professor Max Summers of the Department of Entomology, Texas A & M University, College Station, Tex., 1986. The starting plasmid pAc373 (7.1 kb) is a general baculovirus expression vector having a unique BamHI site immediately downstream from the polyhedron promoter for Autographa californica nuclear polyhedrosis virus (AcNPV). The polyhedron protein is a matrix protein that is nonessential for viral infection and replication in vitro. The plasmid is available from Professor Max Summers of the Department of Entomology, Texas A & M University, College Station, Tex. 77843 and is fully described in Molecular and Cell. Biology, 3(12):2156–2165 (1983).

A. Construction of pAcGPFG

The genes constructed in Examples 2–6 may be used for expression of a chimeric glycoprotein using baculovirus. The plasmid pGPFG-1 will be used in this example. The other chimeric genes are treated as described for pGPFG-1 except when otherwise indicated. Plasmid pGPFG1 is digested with HindIII (pGPFG-3 is digested with HpaII) and the ends are made flush with Klenow enzynme. Synthetic BamHI linkers (New England Biolabs) are ligated to the end of the DNA. The DNA is digested with BamHI and fragment 17 (2.2 kb) containing the gpFG gene is isolated from a gel. The purified fragment is ligated into pAc373 which has been digested with BamHI.

B. Transfection and culturing of *S. Frugiperda*

The gpFG cDNA insert of pAcGPFG is recombined with native AcNPV DNA by cotransfection in S. frugiperda. *S. Frugiperda* (SF9; ATCC CRL 1711) are cultured in Grace Media (Gibco Lab. Livonia, Mich. 48150), 10% fetal calf serum and supplemented with Difco Lactalbumin hydrolysolate and yeastolate. The cells are cotransfected with AcNPV DNA and pAcGPFG at 1 μg/ml and 2 μg/ml respectively. Resulting virus particles are obtained by collecting the media and removing cellular material by low speed centrifugation. The virus containing-media is then used to infect *S. frugiperda*. Subsequent infection of *S. frugiperda* using these viral particles which include both native viral DNA and DNA recombined with the cDNA coding for glycoprotein FG will result in some cells expressing the HRSV protein instead of the polyhedron protein. Purification of recombinant virus is accomplished by a series of limited dilution platings in 96-well tissue culture plates containing *S. frugiperda* cells. Wells containing recombinant virus are detected by dot blot hybridization using pGPFG1 which has been labeled with $^{32}$p-dCTP by nick translation as a probe. Once sufficiently pure, the recombinant virus is detected by its unique occlusion-negative plaque morphology. HRSV protein synthesized in recombinant baculovirus infected cells is detected by Western blot experiments with anti-RSV antibody and $^{125}$I-labeled protein A (Amersham Corp.).

The HRSV protein is purified from the culture media or cells as described in Example 7.

EXAMPLE 10

The Construction of pAcGPFG Containing a Natural Polyhedron Leader Sequence

The plasmid pAc373 described in Example 8 contains a BamHI linker sequence at the −8 position of the polyhedron leader to allow easy insertion of foreign genes. However, this disruption of the polyhedron leader sequence may result in lower levels of expression of the inserted gene than would be possible with the natural polyhedron leader. Described below is a method for linking the natural polyhedron leader sequence to the initiation codon of the HRSV FG gene. The genes constructed in Examples 2-6 may be used in this example for expression of a chimeric glycoprotein. The plasmid pGPFG-1 will be used in this example. The other chimeric genes are treated as described for pGPFG-1.

A. Preparation of pAcGPFG-2

Plasmid pAcGPFG (Example 8) is digested with EcoRV and PstI. EcoRV cleaves the polyhedron leader sequence at position −93 while PstI cleaves the HRSV FG coding sequence at positions +50, +636, and +1701 in the FG coding sequence, and in the pUC12 polylinker region adjacent to the 3'end of the FG gene. The DNA is electrophoresed in a 1% agarose gel and the large fragment (9.8 kb) containing primarily the plasmid pAc373 is purified from the gel.

An oligonucleotide consisting of the polyhedron leader sequence from positions −93 (EcoRV cleavage site) to −1 linked to the FG gene sequence from positions O (nucleotide A of the initiation codon) to +50 (PstI cleavage site) is synthesized and constructed. Because of the length of this sequence, the DNA is synthesized as several oligonucleotides which are then ligated together. The intact oligonucleotide is ligated to the 9.8 kb fragment prepared above. The DNA is transformed into *E. coli HB*101. Clones containing the new plasmid (pAcGPFG-2) are isolated and the newly synthesized region is verified as correct by Maxam-Gilbert sequencing.

B. Inserting the FG gene into pAcGPFG-2

Plasmid pGPFG-1 (Example 2) is partially digested with PstI. PstI cleaves at positions +50, +636, and +1701 in the FG coding sequence, and in the pUC12 polylinker region adjacent to the 3' end of the FG gene. The DNA is electrophoresed in a 1.2% agarose gel. The 2.2 kb fragment corresponding to the nearly intact FG gene (FG position +50 to PstI site in pUC12 polylinker) is purified from the gel. The 2.2 kb fragment is then ligated into plasmid pAcGPFG-2 which had been digested with PstI. The DNA is transformed into E. coli HB101. Clones are isolated and checked for the correct orientation of the FG gene by digestion with EcoRV and SspI which will generate a 2.3 kb fragment. The incorrect orientation will generate a 130 bp fragment. The above gene is inserted into the baculovirus genome for expression of the HRSV chimeric FG glycoprotein as described in Example 8.

EXAMPLE 11

Preparation of a Vaccine

The immunogen can be prepared in vaccine dose form by well-known procedures. The vaccine can be administered intramuscularly, subcutaneously or intranasally. For parenteral administration, such as intramuscular injection, the immunogen may be combined with a suitable carrier, for example, it may be administered in water, saline or buffered vehicles with or without various adjuvants or immunomodulating agents such as aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Propionobacterium acnes), Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.).

The proportion of immunogen and adjuvant can be varied over a broad range so long as both are present in effective amounts. For example, aluminum hydroxide can be present in an amount of about 0.5% of the vaccine mixture ($Al_2O_3$ basis). On a per dose basis, the concentration of the immunogen can range from about 0.015 μg to about 1.5 mg per kilogram per patient body weight. A preferable dosage range is from about 1.5 μg/kg to about 0.15 mg/kg of patient body weight. A suitable dose size in humans is about 0.1-1 ml, preferably about 0.1 ml. Accordingly, a dose for intramuscular injection, for example, would comprise 0.1 ml containing immunogen in admixture with 0.5% aluminum hydroxide.

The vaccine can be administered to pregnant women or to women of child bearing age to stimulate maternal antibodies. The female can be revaccinated as needed. Infants can be vaccinated at 2 to 3 months of age after depletion of maternal antibodies and revaccinated as necessary, preferably at 6 to 9 months of age after maturation of the immune system. Babies born to unvaccinated mothers can be vaccinated at 2 to 3 months of age. The vaccine may also be useful in other susceptible populations such as elderly or infirmed patients.

The vaccine may also be combined with other vaccines for other diseases to produce multivalent vaccines. It may also be combined with other medicaments such as antibiotics.

CHART 1

CONSTRUCTION OF pGPF2

(a) Plasmid pF5-25 is cut with PstI and fragment 1 (1.9 kb) is gel isolated.

Fragment 1

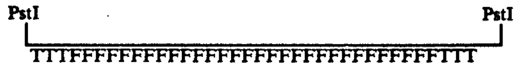

(b) Plasmid pUC12 (2.7 kb) is cut with PstI to yield fragment 2 which is gel isolated.

Fragment 2

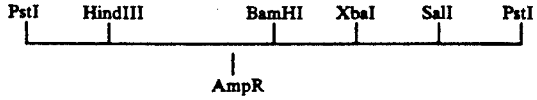

-continued

CHART 1
CONSTRUCTION OF pGPF2

(c) Fragments 1 and 2 are ligated to yield pGPF2 (4.6 kb) which is transformed into *E. coli.*

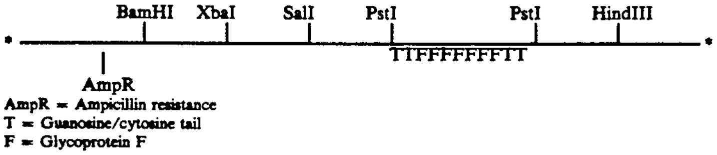

AmpR = Ampicillin resistance
T = Guanosine/cytosine tail
F = Glycoprotein F

CHART 2
CONSTRUCTION OF pGPF3 AND pGPF4

(a) Plasmid pGPF2 is cut with XbaI, treated with bacterial alkaline phosphatase, recut with SalI and treated with Klenow enzyme to yield fragment 3.

Fragment 3

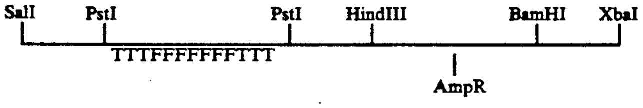

(b) Fragment 3 is digested downstream from the SalI site using lambda exonuclease and the remaining 3' tail is hybridized to the synthetic oligonucleotide complementary to the 5' portion of the leader sequence having the following sequence of GpF cDNA.

5'-end AAATAACAATGGAG (c) The single stranded portion of the cDNA 3' downstream from the synthetic oligonucleotides are filled in using Klenow enzyme and the ends are ligated using T4 ligase to yield pGPF3 (4.6 kb).

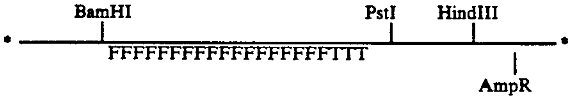

(d) Plasmid pGPF3 is cut with HindIII and treated with Bal 31 to digest the G—C nucleotide tail at the 3' end of the gpF cDNA. The gpF cDNA is cut with BamHI (1.7 kb) isolated from a gel and religated into a BamHI/HincII digestion of PUC12 to yield pGPF4 (4.4 kb).

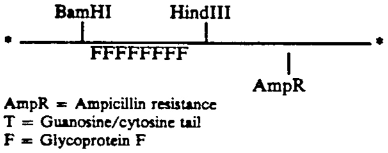

AmpR = Ampicillin resistance
T = Guanosine/cytosine tail
F = Glycoprotein F

CHART 3
CONSTRUCTION OF A
CHIMERIC FG GLYCOPROTEIN GENE

Plasmid G2B-16

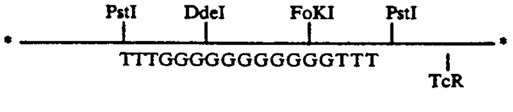

(a) Plasmid G2B-16 is digested with DdeI and FoKI, and the ends are made blunt with Klenow enzyme. The DNA is electrophoresed in a 1.5% agarose gel and fragment 4 (550 bp) is purified from the agarose.

Fragment 4 GGGGGGGGGGG (b) Plasmid pGPF-4 (Chart 2) is digested with NsiI. The ends are made blunt with T4 DNA polymerase and dephosphorylated with bacterial alkaline phosphatase. Fragment 4 is then ligated into the plasmid to form pGPFG-1 (5.0 kb).

Plasmid GPFG-1

-continued

CHART 3
CONSTRUCTION OF A
CHIMERIC FG GLYCOPROTEIN GENE

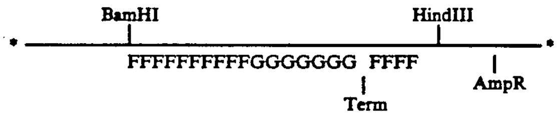

AmpR = Ampicillin resistance
TcR = Tetracycline resistance
T = Guanosine/Cytosine tail
G = DNA sequences for G glycoprotein
F = DNA sequences for F glycoprotein
Term = Translational termination signal

CHART 4
USING LINKERS TO
ADJUST THE READING FRAME OF FG

Plasmid G2B-16

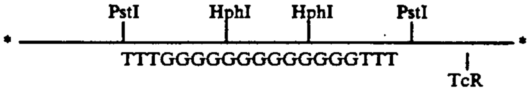

-continued

CHART 4
USING LINKERS TO
ADJUST THE READING FRAME OF FG

SalI Linker CGGTCGACCG
GCCAGCTGGC (a) Plasmid G2B-16 is digested with HphI and the ends are made blunt with T4 DNA polymerase. The SalI linker is ligated to the ends of the cDNA. The DNA is digested with SalI and fragment 5 (410 bp) is gel purified.

Fragment 5
LGGGGGGGGGGGGGGGGGL (b) Plasmid GPF4 (Chart 2) is digested with NsiI and the ends are made blunt with T4 DNA polymerase. The SalI linker is ligated to the ends of the cDNA. The DNA is digested with SalI and the plasmid (4.4 kb) is gel purified. Fragment 5 is then ligated to the gel purified GPF4 to form pGPFG-2.

Plasmid GPFG-2
BamHI HindIII
FFFFFFFFLGGGGGGLFFFFF
Term AmpR

AmpR = Ampicillin resistance
TcR = Tetracycline resistance
T = Guanidine/Cytosine tail
F = DNA sequences for F glycoprotein
G = DNA sequences for G glycoprotein
L = SalI linker
Term = Translational Termination Signal

CHART 5
USING OLIGONUCLEOTIDES TO
GENERATE FG GENES OF VARIOUS LENGTHS (a) Oligonucleotide A consists of oligonucleotide 1 (36 bp) or oligonucleotides 1 and 2 ligated together (81 bp). Oligonucleotide B consists of oligonucleotide 3 (80 bp) or oligonucleotides 3 and 4 ligated together (164 bp). Oligonucleotide C consists of oligonucleotide 5 (60 bp), or oligonucleotide 5 and 6 ligated together (120 bp) or oligonucleotides 5, 6, and 7 ligated together (189 bp), or oligonucleotides 5, 6, 7, and 8 ligated together (258 bp). Oligonucleotides A, B, and C are gel purified.

| Oligonucleotide A | Oligonucleotide B | Oligonucleotide C |
|---|---|---|
| 1111111 | 333333 | 5555 |
| 11111111222222 | 3333333444444 | 55556666 |
| | | 555566667777 |
| | | 5555666677778888 |

(b) Plasmid GPF-4 is digested with NsiI and oligonucleotide A is ligated into the NsiI site. The DNA is digested with HindIII and the plasmid is religated to form pGPF-5.

Plasmid GPF-5
BamHI NsiI HindIII
FFFFFFFFFFAAAA
AmpR (c) Plasmid G2B-16 is digested with HinfI and XhoII, and fragment 6 (277 bp) is gel purified.

Fragment 6
HinfI XhoII
GGGGGGGGGGG (d) Oligonucleotides B and C are ligated to fragment 6. The DNA is digested with HindIII and fragment 7 is gel purified (length of fragment 7 varies from 417 bp to 700 bp depending on oligonucleotides contained within oligonucleotides B and C).

-continued

CHART 5
USING OLIGONUCLEOTIDES TO
GENERATE FG GENES OF VARIOUS LENGTHS

Fragment 7
HindIII HinfI XhoII HindIII
BBBBGGGGGCCCCC (e) Plasmid GPF-5 is digested with HindIII and dephosphorylated with bacterial alkaline phosphatase. Fragment 7 is then ligated into the HindIII site of pGPF-5 to form pGPFG-3.

Plasmid GPFG-3
HindIII HindIII HindIII HpaII
FFFFFFFFAAABBGGGGCC
Term AmpR

AmpR = Ampicillin resistance
F = DNA sequences for F glycoprotein
G = DNA sequences for G glycoprotein
A = Oligonucleotide A
B = Oligonucleotide B
C = Oligonucleotide C
Term = Translational Termination Signal

CHART 6
CONSTRUCTION OF AN FG GENE
CONTAINING AN ANCHOR REGION

Plasmid G2B-16
PstI DdeI FoKI PstI
TTTGGGGGGGGGGGGTTT
TcR (a) Plasmid G2B-16 is digested with DdeI and FoKI. Oligonucleotides 9 and 10 are ligated to the ends of the DNA. The DNA is digested with NsiI and fragment 8 (550 bp) is gel purified.

Fragment 8
NsiI NsiI
9 GGGGGGGGGG 10

(b) Plasmid GPF-4 is digested with NsiI and fragment 8 is ligated into the NsiI site to form pGPFG-4.

Plasmid GPFG-4
BamHI HindIII
FFFFFFFF9GGGGGG10AAAA
Term AmpR

AmpR = Ampicillin resistance
TcR = Tetracycline resistance
T = Guanosine/Cytosine tail
F = DNA sequences for F glycoprotein
G = DNA sequences for G glycoprotein
9 = Oligonucleotide 9
10 = Oligonucleotide 10
A = DNA sequences coding for anchor region of F glycoprotein
Term = Translational Termination Signal

CHART 7
PREPARATION OF G GENE FOR
CONSTRUCTION OF GF CHIMERIC GENE

Plasmid G2B-16
PstI NlaIII FoKI PstI
TTTGGGGGGGGGGGGTTT
TcR (a) Plasmid G2B-16 is digested with NlaIII and FoKI. Oligonucleotides 11 and 12 are ligated to the ends of the DNA and fragment 9 (850 bp) is gel purified.

-continued

CHART 7

PREPARATION OF G GENE FOR CONSTRUCTION OF GF CHIMERIC GENE

Fragment 9

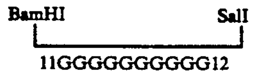

(b) Plasmid pUC12 is digested with BamHI and SalI, and dephorylated with bacterial alkaline phosphatase. Fragment 9 is ligated into the plasmid to form pGPG-1.

Plasmid GPG-1

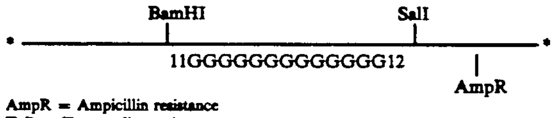

AmpR = Ampicillin resistance
TcR = Tetracycline resistance
T = Guanosine/Cytosine tail
G = DNA sequences for G glycoprotein
11 = Oligonucleotide 11
12 = Oligonucleotide 12

CHART 8

INSERTION OF G cDNA INTO pGPG-1

Plasmid F5-25

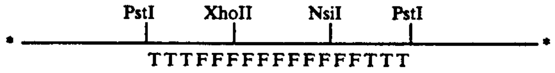

-continued

CHART 8

INSERTION OF G cDNA INTO pGPG-1

(a) Plasmid F5-25 is digested with XhoII and NsiI. Oligonucleotides 13 and 14 are ligated to the ends of the DNA. The DNA is digested with SalI and fragment 10 (960 bp) is gel purified.

Fragment 10

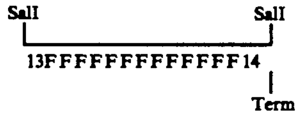

(b) PGPF-1 is digested with SalI and dephosphorylated with bacterial alkaline phosphatase. Fragment 10 is then ligated into the plasmid to form pGPGF-1.

Plasmid GPGF-1

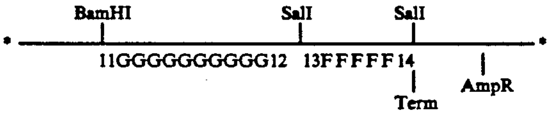

AmpR = Ampicillin resistance
TcR = Tetracycline resistance
T = Guanosine/Cytosine tail
G = DNA sequences coding for G glycoprotein
F = DNA sequences coding for F glycoprotein
11 = Oligonucleotide 11
12 = Oligonucleotide 12
13 = Oligonucleotide 13
14 = Oligonucleotide 14
Term = Translational Termination Signal

CHART 9

GLYCOPROTEIN FG

| | | | | | | | | | | | | | | | | |
|---|---|---|---|---|---|---|---|---|---|---|---|---|---|---|---|---|
| 1 | Met | Glu | Leu | Leu | Ile | Leu | Lys | Ala | Asn | Ala | Ile | Thr | Thr | Ile | Leu | Thr |
| 17 | Ala | Val | Thr | Phe | Cys | Phe | Ala | Ser | Gly | Gln | Asn | Ile | Thr | Glu | Glu | Phe |
| 33 | Tyr | Gln | Ser | Thr | Cys | Ser | Ala | Val | Ser | Lys | Gly | Tyr | Leu | Ser | Ala | Leu |
| 49 | Arg | Thr | Gly | Trp | Tyr | Thr | Ser | Val | Ile | Thr | Ile | Glu | Leu | Ser | Asn | Ile |
| 65 | Lys | Glu | Asn | Lys | Cys | Asn | Gly | Thr | Asp | Ala | Lys | Val | Lys | Leu | Ile | Lys |
| 81 | Gln | Glu | Leu | Asp | Lys | Tyr | Lys | Asn | Ala | Val | Thr | Glu | Leu | Gln | Leu | Leu |
| 97 | Met | Gln | Ser | Thr | Pro | Pro | Thr | Asn | Asn | Arg | Ala | Arg | Arg | Glu | Leu | Pro |
| 113 | Arg | Phe | Met | Asn | Tyr | Thr | Leu | Asn | Asn | Ala | Lys | Lys | Thr | Asn | Val | Thr |
| 129 | Leu | Ser | Lys | Lys | Arg | Lys | Arg | Arg | Phe | Leu | Gly | Phe | Leu | Leu | Gly | Gly |
| 145 | Gly | Ser | Ala | Ile | Ala | Ser | Gly | Val | Ala | Val | Ser | Lys | Val | Leu | His | Leu |
| 161 | Glu | Gly | Glu | Val | Asn | Lys | Ile | Lys | Ser | Ala | Leu | Leu | Ser | Thr | Asn | Lys |
| 177 | Ala | Val | Val | Ser | Leu | Ser | Asn | Gly | Val | Ser | Val | Leu | Thr | Ser | Lys | Val |
| 193 | Leu | Asp | Leu | Lys | Asn | Tyr | Ile | Asp | Lys | Gln | Leu | Leu | Pro | Ile | Val | Asn |
| 209 | Lys | Gln | Ser | Cys | Ser | Ile | Ser | Asn | Ile | Glu | Thr | Val | Ile | Glu | Phe | Gln |
| 225 | Gln | Lys | Asn | Asn | Arg | Leu | Leu | Glu | Ile | Thr | Arg | Glu | Phe | Ser | Val | Asn |
| 241 | Ala | Gly | Val | Thr | Thr | Pro | Val | Ser | Thr | Tyr | Met | Leu | Thr | Asn | Ser | Glu |
| 257 | Leu | Leu | Ser | Leu | Ile | Asn | Asp | Met | Pro | Ile | Thr | Asn | Asp | Gln | Lys | Lys |
| 273 | Leu | Met | Ser | Asn | Asn | Val | Gln | Ile | Val | Arg | Gln | Gln | Ser | Tyr | Ser | Ile |
| 289 | Met | Ser | Ile | Ile | Lys | Glu | Glu | Val | Leu | Ala | Tyr | Val | Val | Gln | Leu | Pro |
| 305 | Leu | Tyr | Gly | Val | Ile | Asp | Thr | Pro | Cys | Trp | Lys | Leu | His | Thr | Ser | Pro |
| 321 | Leu | Cys | Thr | Thr | Asn | Thr | Lys | Glu | Gly | Ser | Asn | Ile | Cys | Leu | Thr | Arg |
| 337 | Thr | Asp | Arg | Gly | Trp | Tyr | Cys | Asp | Asn | Ala | Gly | Ser | Val | Ser | Phe | Phe |
| 353 | Pro | Gln | Ala | Glu | Thr | Cys | Lys | Val | Gln | Ser | Asn | Arg | Val | Phe | Cys | Asp |
| 369 | Thr | Met | Asn | Ser | Leu | Thr | Leu | Pro | Ser | Glu | Ile | Asn | Leu | Cys | Asn | Val |
| 385 | Asp | Ile | Phe | Asn | Pro | Lys | Tyr | Asp | Cys | Lys | Ile | Met | Thr | Ser | Lys | Thr |
| 401 | Asp | Val | Ser | Ser | Ser | Val | Ile | Thr | Ser | Leu | Gly | Ala | Ile | Val | Ser | Cys |
| 417 | Tyr | Gly | Lys | Thr | Lys | Cys | Thr | Ala | Ser | Asn | Lys | Asn | Arg | Gly | Ile | Ile |
| 433 | Lys | Thr | Phe | Ser | Asn | Gly | Cys | Asp | Tyr | Val | Ser | Asn | Lys | Gly | Met | Asp |
| 449 | Thr | Val | Ser | Val | Gly | Asn | Thr | Leu | Tyr | Tyr | Val | Asn | Lys | Gln | Glu | Gly |
| 465 | Lys | Ser | Leu | Tyr | Val | Lys | Gly | Glu | Pro | Ile | Ile | Asn | Phe | Tyr | Asp | Pro |
| 481 | Leu | Val | Phe | Pro | Ser | Asp | Glu | Phe | Asp | Gln | Leu | Gly | Ile | Ser | Pro | Ser |
| 497 | Asn | Pro | Ser | Glu | Ile | Thr | Ser | Gln | Ile | Thr | Thr | Ile | Leu | Ala | Ser | Thr |
| 513 | Thr | Pro | Gly | Val | Lys | Ser | Thr | Leu | Gln | Ser | Thr | Thr | Val | Lys | Thr | Lys |
| 529 | Asn | Thr | Thr | Thr | Thr | Gln | Thr | Gln | Pro | Ser | Lys | Pro | Thr | Thr | Lys | Gln |
| 545 | Arg | Gln | Asn | Lys | Pro | Pro | Ser | Lys | Pro | Asn | Asn | Asp | Phe | His | Phe | Glu |
| 561 | Val | Phe | Asn | Phe | Val | Pro | Cys | Ser | Ile | Cys | Ser | Asn | Asn | Pro | Thr | Cys |
| 577 | Trp | Ala | Ile | Cys | Lys | Arg | Ile | Pro | Asn | Lys | Lys | Pro | Gly | Lys | Lys | Thr |
| 593 | Thr | Thr | Lys | Pro | Thr | Lys | Lys | Pro | Thr | Leu | Lys | Thr | Thr | Lys | Lys | Asp |
| 609 | Pro | Lys | Pro | Gln | Thr | Thr | Lys | Ser | Lys | Glu | Val | Pro | Thr | Thr | Lys | Pro |
| 625 | Thr | Glu | Glu | Pro | Thr | Ile | Asn | Thr | Thr | Lys | Thr | Asn | Ile | Ile | Thr | Thr |
| 641 | Leu | Leu | Thr | Ser | Asn | Thr | Thr | Gly | Asn | Pro | Glu | Leu | Thr | Ser | Gln | Met |
| 657 | Glu | Thr | Phe | His | Ser | Thr | Ser | Ser | Glu | Gly | Asn | Pro | Ser | Pro | Ser | Gln |
| 673 | Val | Asn | Ile | Ser | Ser | Gln | Arg | Glu | Asp | | | | | | | |

I claim:

1. A polypeptide comprising at least one immunogenic fragment from both human respiratory syncytial virus glycoproteins F and G.

2. A polypeptide according to claim 1, additionally comprising a signal sequence from glycoprotein F.

3. A polypeptide according to claim 2, which is, beginning with the N terminal end, the signal sequence from glycoprotein F, an immunogenic fragment of glycoprotein F and an immunogenic fragment of glycoprotein G.

4. A polypeptide according to claim 1, which is

| | | | | | | | | | | | | | | | | |
|---|---|---|---|---|---|---|---|---|---|---|---|---|---|---|---|---|
| 1 | Met | Glu | Leu | Leu | Ile | Leu | Lys | Ala | Asn | Ala | Ile | Thr | Thr | Ile | Leu | Thr |
| 17 | Ala | Val | Thr | Phe | Cys | Phe | Ala | Ser | Gly | Gln | Asn | Ile | Thr | Glu | Glu | Phe |
| 33 | Tyr | Gln | Ser | Thr | Cys | Ser | Ala | Val | Ser | Lys | Gly | Tyr | Leu | Ser | Ala | Leu |
| 49 | Arg | Thr | Gly | Trp | Tyr | Thr | Ser | Val | Ile | Thr | Ile | Glu | Leu | Ser | Asn | Ile |
| 65 | Lys | Glu | Asn | Lys | Cys | Asn | Gly | Thr | Asp | Ala | Lys | Val | Lys | Leu | Ile | Lys |
| 81 | Gln | Glu | Leu | Asp | Lys | Tyr | Lys | Asn | Ala | Val | Thr | Glu | Leu | Gln | Leu | Leu |
| 97 | Met | Gln | Ser | Thr | Pro | Pro | Thr | Asn | Asn | Arg | Ala | Arg | Arg | Glu | Leu | Pro |
| 113 | Arg | Phe | Met | Asn | Tyr | Thr | Leu | Asn | Asn | Ala | Lys | Lys | Thr | Asn | Val | Thr |
| 129 | Leu | Ser | Lys | Lys | Arg | Lys | Arg | Arg | Phe | Leu | Gly | Phe | Leu | Leu | Gly | Gly |
| 145 | Gly | Ser | Ala | Ile | Ala | Ser | Gly | Val | Ala | Val | Ser | Lys | Val | Leu | His | Leu |
| 161 | Glu | Gly | Glu | Val | Asn | Lys | Ile | Lys | Ser | Ala | Leu | Leu | Ser | Thr | Asn | Lys |
| 177 | Ala | Val | Val | Ser | Leu | Ser | Asn | Gly | Val | Ser | Val | Leu | Thr | Ser | Lys | Val |
| 193 | Leu | Asp | Leu | Lys | Asn | Tyr | Ile | Asp | Lys | Gln | Leu | Leu | Pro | Ile | Val | Asn |
| 209 | Lys | Gln | Ser | Cys | Ser | Ile | Ser | Asn | Ile | Glu | Thr | Val | Ile | Glu | Phe | Gln |
| 225 | Gln | Lys | Asn | Asn | Arg | Leu | Leu | Glu | Ile | Thr | Arg | Glu | Phe | Ser | Val | Asn |
| 241 | Ala | Gly | Val | Thr | Thr | Pro | Val | Ser | Thr | Tyr | Met | Leu | Thr | Asn | Ser | Glu |
| 257 | Leu | Leu | Ser | Leu | Ile | Asn | Asp | Met | Pro | Ile | Thr | Asn | Asp | Gln | Lys | Lys |
| 273 | Leu | Met | Ser | Asn | Asn | Val | Gln | Ile | Val | Arg | Gln | Gln | Ser | Tyr | Ser | Ile |
| 289 | Met | Ser | Ile | Ile | Lys | Glu | Glu | Val | Leu | Ala | Tyr | Val | Val | Gln | Leu | Pro |
| 305 | Leu | Tyr | Gly | Val | Ile | Asp | Thr | Pro | Cys | Trp | Lys | Leu | His | Thr | Ser | Pro |
| 321 | Leu | Cys | Thr | Thr | Asn | Thr | Lys | Glu | Gly | Ser | Asn | Ile | Cys | Leu | Thr | Arg |
| 337 | Thr | Asp | Arg | Gly | Trp | Tyr | Cys | Asp | Asn | Ala | Gly | Ser | Val | Ser | Phe | Phe |
| 353 | Pro | Gln | Ala | Glu | Thr | Cys | Lys | Val | Gln | Ser | Asn | Arg | Val | Phe | Cys | Asp |
| 369 | Thr | Met | Asn | Ser | Leu | Thr | Leu | Pro | Ser | Glu | Ile | Asn | Leu | Cys | Asn | Val |
| 385 | Asp | Ile | Phe | Asn | Pro | Lys | Tyr | Asp | Cys | Lys | Ile | Met | Thr | Ser | Lys | Thr |
| 401 | Asp | Val | Ser | Ser | Ser | Val | Ile | Thr | Ser | Leu | Gly | Ala | Ile | Val | Ser | Cys |
| 417 | Tyr | Gly | Lys | Thr | Lys | Cys | Thr | Ala | Ser | Asn | Lys | Asn | Arg | Gly | Ile | Ile |
| 433 | Lys | Thr | Phe | Ser | Asn | Gly | Cys | Asp | Tyr | Val | Ser | Asn | Lys | Gly | Met | Asp |
| 449 | Thr | Val | Ser | Val | Gly | Asn | Thr | Leu | Tyr | Tyr | Val | Asn | Lys | Gln | Glu | Gly |
| 465 | Lys | Ser | Leu | Tyr | Val | Lys | Gly | Glu | Pro | Ile | Ile | Asn | Phe | Tyr | Asp | Pro |
| 481 | Leu | Val | Phe | Pro | Ser | Asp | Glu | Phe | Asp | Gln | Leu | Gly | Ile | Ser | Pro | Ser |
| 497 | Asn | Pro | Ser | Glu | Ile | Thr | Ser | Gln | Ile | Thr | Thr | Ile | Leu | Ala | Ser | Thr |
| 513 | Thr | Pro | Gly | Val | Lys | Ser | Thr | Leu | Gln | Ser | Thr | Thr | Val | Lys | Thr | Lys |
| 529 | Asn | Thr | Thr | Thr | Thr | Gln | Thr | Gln | Pro | Ser | Lys | Pro | Thr | Thr | Lys | Gln |
| 545 | Arg | Gln | Asn | Lys | Pro | Pro | Ser | Lys | Pro | Asn | Asn | Asp | Phe | His | Phe | Glu |
| 561 | Val | Phe | Asn | Phe | Val | Pro | Cys | Ser | Ile | Cys | Ser | Asn | Asn | Pro | Thr | Cys |
| 577 | Trp | Ala | Ile | Cys | Lys | Arg | Ile | Pro | Asn | Lys | Lys | Pro | Gly | Lys | Lys | Thr |
| 593 | Thr | Thr | Lys | Pro | Thr | Lys | Lys | Pro | Thr | Leu | Lys | Thr | Thr | Lys | Lys | Asp |
| 609 | Pro | Lys | Pro | Gln | Thr | Thr | Lys | Ser | Lys | Glu | Val | Pro | Thr | Thr | Lys | Pro |
| 625 | Thr | Glu | Glu | Pro | Thr | Ile | Asn | Thr | Thr | Lys | Thr | Asn | Ile | Ile | Thr | Thr |
| 641 | Leu | Leu | Thr | Ser | Asn | Thr | Thr | Gly | Asn | Pro | Glu | Leu | Thr | Ser | Gln | Met |
| 657 | Glu | Thr | Phe | His | Ser | Thr | Ser | Ser | Glu | Gly | Asn | Pro | Ser | Pro | Ser | Gln |
| 673 | Val | Asn | Ile | Ser | Ser | Gln | Arg | Glu | Asp. | | | | | | | |

* * * * *